(12) United States Patent
Thomas

(10) Patent No.: US 12,319,890 B2
(45) Date of Patent: Jun. 3, 2025

(54) RAPID BOTANICAL OIL DISTILLATION DEVICE UTILIZING MICROWAVE AGENT

(71) Applicant: Natural Extraction Systems, LLC, Boulder, CO (US)

(72) Inventor: C. Russell Thomas, Boulder, CO (US)

(73) Assignee: Natural Extraction Systems, LLC, Boulder, CO (US)

( * ) Notice: Subject to any disclaimer, the term of this patent is extended or adjusted under 35 U.S.C. 154(b) by 0 days.

(21) Appl. No.: 18/515,005

(22) Filed: Nov. 20, 2023

(65) Prior Publication Data

US 2024/0343991 A1    Oct. 17, 2024

Related U.S. Application Data

(63) Continuation of application No. 17/333,728, filed on May 28, 2021, now Pat. No. 11,820,959, which is a
(Continued)

(51) Int. Cl.
| | | |
|---|---|---|
| *C11B 1/04* | (2006.01) | |
| *A61K 36/185* | (2006.01) | |

(Continued)

(52) U.S. Cl.
CPC .............. *C11B 1/10* (2013.01); *A61K 36/185* (2013.01); *A61K 41/00* (2013.01); *B01D 3/106* (2013.01);
(Continued)

(58) Field of Classification Search
CPC ..... C11B 1/10; C11B 1/04; C11B 1/02; C11B 1/12; C11B 3/005; C11B 3/12;
(Continued)

(56) References Cited

U.S. PATENT DOCUMENTS 5,338,557 A * 8/1994 Pare ........................ C11B 9/025
426/430
7,001,629 B1 * 2/2006 Mengal ............... B01D 11/0211
426/442
(Continued)

FOREIGN PATENT DOCUMENTS

CN            1061729 A * 6/1992 ............ B01D 11/02
CN          103073737 A * 5/2013
(Continued)

OTHER PUBLICATIONS

English Translation of Publication CN 1061729A, published Jun. 10, 1992 (Year: 1992).*
(Continued)

*Primary Examiner* — Joseph W Drodge
(74) *Attorney, Agent, or Firm* — Douglas G. Metcalf

(57) ABSTRACT

Various aspects of the disclosure relate to methods and systems for extracting plant oil from plant material. A system may comprise a microwave emitter, an extraction chamber, and a cooling chamber. Microwave radiation emitted by the microwave emitter may dielectrically heat a microwave absorbing agent, which may heat the plant oil of the plant material. Plant oil of the plant material may be volatized in the extraction chamber and may be directed into the cooling chamber to be condensed.

20 Claims, 1 Drawing Sheet

Related U.S. Application Data continuation of application No. 16/465,735, filed as application No. PCT/US2017/064257 on Dec. 1, 2017, now Pat. No. 11,021,674.

(60) Provisional application No. 62/428,868, filed on Dec. 1, 2016.

(51) Int. Cl.

| | |
|---|---|
| *A61K 41/00* | (2020.01) |
| *B01D 3/10* | (2006.01) |
| *B01D 3/40* | (2006.01) |
| *B01D 5/00* | (2006.01) |
| *B01D 11/02* | (2006.01) |
| *C11B 1/10* | (2006.01) |

(52) U.S. Cl.
CPC ............... *B01D 3/40* (2013.01); *B01D 5/006* (2013.01); *B01D 11/028* (2013.01); *B01D 11/0288* (2013.01); *C11B 1/04* (2013.01)

(58) Field of Classification Search
CPC . C11B 1/106; C11B 1/14; C11B 1/108; C11B 3/006; A61K 36/185; A61K 41/00; A61K 2236/00; A61K 2236/30; A61K 2236/333; A61K 2236/39; A61K 2236/50; A61K 2236/51; B01D 3/106; B01D 3/40; B01D 5/006; B01D 11/028; B01D 11/0288; B01D 5/00; B01D 11/00; B01D 5/0033; B01D 11/0265; B01D 1/00; B01D 1/0064; B01D 3/06; B01D 5/0057; B01D 11/02; B01D 11/04; B01D 11/0484; B01D 11/0488; B01D 11/0492; B01D 2257/702; A61P 25/18
USPC ........ 210/634, 638, 639, 774; 554/8, 12, 20, 554/175
See application file for complete search history.

(56) References Cited

U.S. PATENT DOCUMENTS

| | | | | |
|---|---|---|---|---|
| 11,021,674 | B2* | 6/2021 | Thomas | ................... C11B 1/02 |
| 11,820,959 | B2* | 11/2023 | Thomas | ............. B01D 11/0288 |
| 2004/0187340 | A1* | 9/2004 | Chemat | ............. B01D 11/0296 |
| | | | | 34/259 |
| 2011/0219679 | A1* | 9/2011 | Budarin | .................... C10C 5/00 |
| | | | | 422/186 |
| 2011/0233203 | A1* | 9/2011 | Visinoni | ................... A23L 5/00 |
| | | | | 219/756 |
| 2013/0240347 | A1* | 9/2013 | Hackleman | .............. B01D 3/40 |
| | | | | 202/185.1 |
| 2014/0298511 | A1* | 10/2014 | Lewis | .................. A61K 36/185 |
| | | | | 800/298 |
| 2015/0147489 | A1* | 5/2015 | Mottin | .................... B23P 6/007 |
| | | | | 118/620 |
| 2015/0224422 | A1* | 8/2015 | Dabao | ................ B01D 11/0296 |
| | | | | 422/280 |
| 2016/0051510 | A1* | 2/2016 | Allen | .................... A61K 31/352 |
| | | | | 424/443 |
| 2016/0053199 | A1* | 2/2016 | Clodoveo | ............... C11B 1/108 |
| | | | | 554/8 |
| 2016/0250270 | A1* | 9/2016 | Wendschuh | ......... A61K 31/015 |
| | | | | 514/454 |
| 2016/0324909 | A1* | 11/2016 | Scialdone | ............ A61K 31/192 |
| 2017/0008870 | A1* | 1/2017 | Dibble | ................. C07D 311/80 |
| 2018/0000857 | A1* | 1/2018 | Kotra | ....................... A61P 25/00 |
| 2019/0192601 | A1* | 6/2019 | Díaz Rebolledo | ..... A61K 35/60 |

FOREIGN PATENT DOCUMENTS

| | | | | |
|---|---|---|---|---|
| CN | 105125665 A | * | 12/2015 | |
| EP | 0485668 B1 | * | 1/1996 | ............... C11B 9/02 |
| FR | 2742358 A1 | | 6/1997 | |

OTHER PUBLICATIONS

English translation of Patent Publication CN 103073737A, published May 1, 2013. (Year: 2013).*
English translation of Patent Publication CN 105125665A, published Oct. 11, 2015. (Year: 2015).*
Filly, A. et al., Solvent-free microwave extraction of essential oil from aromatic herbs: From laboratory pilot industrial scale. Food Chemistry 150(2014); 193-198.
Petrov, V.M. et al. Microwave Absorbing Materials. Inorganic Materials vol. 37, No. 2, 2001, pp. 93-98.
Wang, Z. et al. Improved solvent-free microwave extraction of essential oil from dried *Cuminum cyminum* L. and Zanthoxylum bungeanum Maxim. Journal of Chromatography A, 1102 (2006) 11-17.
Benmoussa, H. et al. Enhanced solvent-free microwave extraction of Foeniculum vulgare Mill. essential oil seeds using double walled reactor. Arabian Journal of Chemistry (2019) 12, 3863-3870.

* cited by examiner

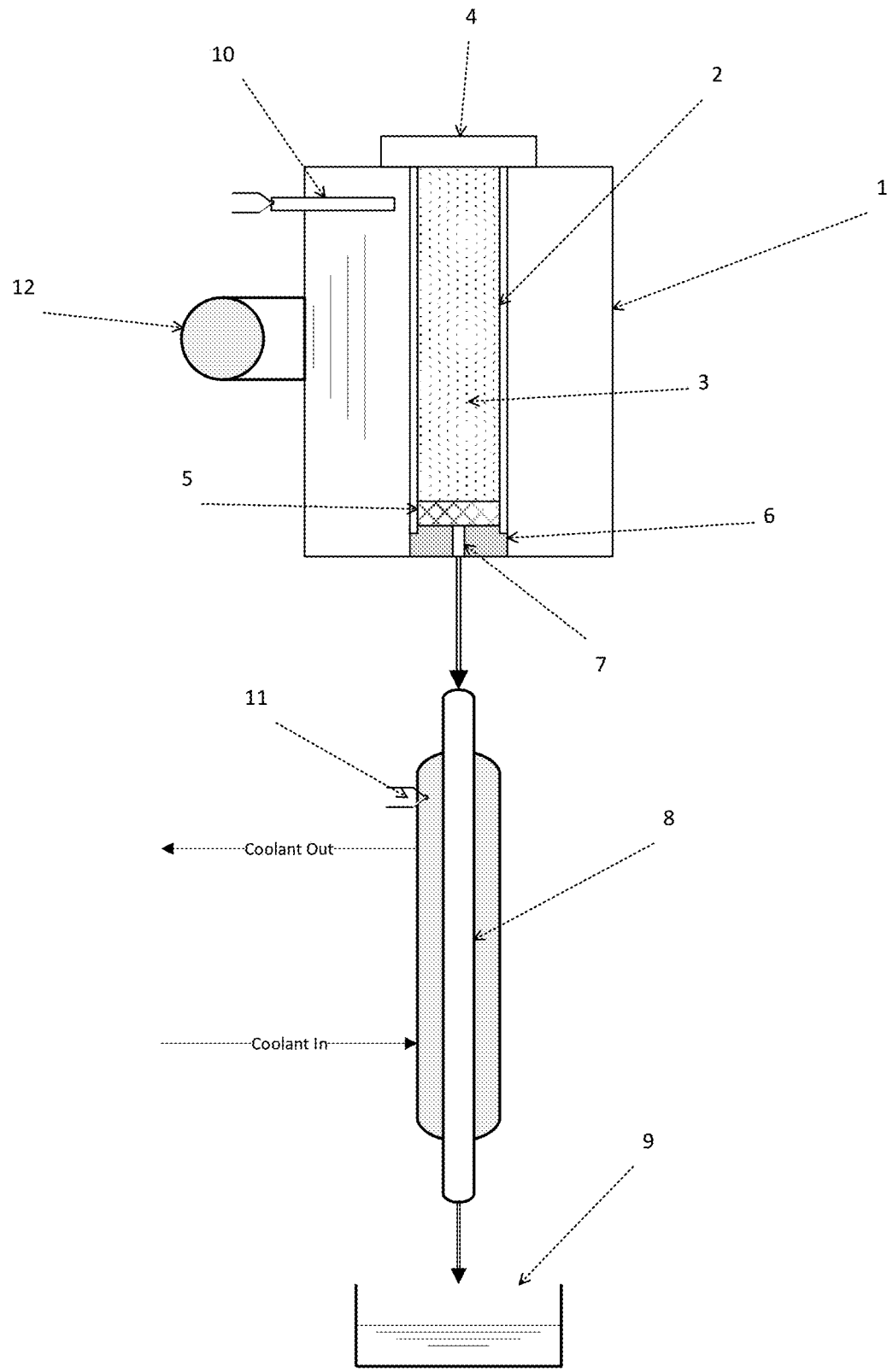

RAPID BOTANICAL OIL DISTILLATION DEVICE UTILIZING MICROWAVE AGENT

CROSS REFERENCE TO RELATED APPLICATION

This application is a continuation of U.S. patent application Ser. No. 17/333,728, which granted as U.S. Pat. No. 11,820,959, and which is a continuation of U.S. patent application Ser. No. 16/465,735, which granted as U.S. Pat. No. 11,021,674, and which is the U.S. national stage under 35 U.S.C. § 371 of International Application no. PCT/US2017/064257, which claims priority to U.S. provisional patent application No. 62/428,868, filed Dec. 1, 2016, each of which is incorporated by reference in its entirety.

BACKGROUND

Microwaves have been effectively utilized to steam distill volatile essential oils from plant materials. However, microwaves have not been able to effectively steam distill cannabinoid oils or heavy oleoresins from plant material. The use of microwaves to directly heat dry plant materials to evaporate and distill high boiling point plant oils and oleoresins has also not been proven effective, since most plant oils are predominantly non-polar molecules and do not efficiently absorb microwaves. Attempts to distill oleoresins with microwaves often results in combustion of the plant material prior to evaporating the desired oils, or it very ineffectively evaporates the oleoresins while subjecting the plant oils and oeloresins to heat degradation. A more effective microwave distillation method is therefore desirable.

SUMMARY OF THE INVENTION

This invention provides a method to rapidly and evenly heat the oils and oleoresins within plant material by mixing or contacting the plant material with a microwave absorbing agent. By using this microwave agent, the plant oils are rapidly heated, volatilized, and distilled without causing thermal breakdown of the distilled oils.

Various aspects of the invention relate to a method of extracting oil from plant material. The method may comprise providing a system for extracting oil from plant material. The system may comprise (a) a microwave emitter, (b) an extraction chamber in communication with the microwave emitter such that microwave radiation emitted by the microwave emitter is directed into the extraction chamber, and (c) a cooling chamber in communication with the extraction chamber such that volatized oil in the extraction chamber is directed into the cooling chamber.

The method may further comprise combining a plant material and a microwave absorbing agent; inserting the plant material and the microwave absorbing agent into the extraction chamber; irradiating the microwave absorbing agent with microwave radiation emitted from the microwave emitter, thereby dielectrically heating the microwave absorbing agent and/or heating the microwave absorbing agent by interfacial or Maxwell-Wagner-Sillars polarization, heating the plant material, and volatizing a plant oil from the plant material to produce a volatized oil; condensing the volatized oil in the cooling chamber, thereby producing a condensed oil; and collecting a portion of the condensed oil, thereby producing a collected oil that is suitable for human consumption. The plant material may be heated primarily by heat transfer from the microwave absorbing agent to the plant material, e.g., by thermal radiation or convection, rather than by dielectric heating of the plant material.

The microwave absorbing agent may consist of various types of non-polar substrates or substrates containing non-polar molecules, substrates containing ions or dipole molecules, or may consist of any other substance or substrate that is excited by microwaves or electromagnetic radiation so long as either (1) the microwave absorbing agent and any microwave absorbing composition are not both food or (2) either the microwave absorbing agent or any microwave absorbing composition is used in an amount that is substantially greater than an amount used in the microwave-preparation of food (i.e., the microwave absorbing agent or any microwave absorbing composition is used in an amount that is at least 10-fold greater than an amount used in the microwave-preparation of food relative to the amount of plant material, e.g., silica may be added to food as an anti-caking agent, for example, but the addition of 100 grams of silica as a microwave absorbing agent to 100 grams of plant material presents an amount of silica that is substantially greater than an amount of silica used in the microwave-preparation of any food), and (3) the microwave absorbing agent allows the plant material to be heated above the relative boiling point of water (i.e., wherein the relative boiling point of water is the boiling point of water relative to the pressure within an extraction chamber or removable cartridge and relative to the combined vapor pressure of volatile species within the extraction chamber or removable cartridge, respectively, e.g., in light of any boiling-point elevation).

Combining the plant material with the microwave absorbing agent may comprise combining the plant material with a microwave absorbing composition comprising the microwave absorbing agent. The microwave absorbing composition may comprise, for example, a mixture of solids as described herein, e.g., and at least some solids of the mixture of solids may comprise the microwave absorbing agent. The solids of the mixture of solids may be sized, for example, from about 0.1 µm to about 5 cm such as about 0.1 µm to about 100 µm, about 1 µm to about 1 mm, about 10 µm to about 10 mm, about 100 µm to about 50 mm, about 0.1 µm to about 10 µm, about 1 µm to about 100 µm, about 10 µm to about 1 mm, about 100 µm to about 10 mm, about 1 mm to about 50 mm, about 0.1 µm to about 1 µm, about 0.5 µm to about 5 µm, about 1 µm to about 10 µm, about 5 µm to about 50 µm, about 10 µm, to about 100 µm, about 50 µm to about 500 µm, about 100 µm to about 1 mm, about 500 µm to about 5 mm, about 1 mm to about 1 cm, or about 5 mm to about 5 cm. The mixture of solids may be a powder or grit or may comprise beads or raschig rings, fibers, rods or sheets or forms of structured packing. The mixture of solids may comprise metal, glass, ceramic, and/or clay. In some embodiments, the glass, ceramic, or clay may be impregnated substances that consist of polar molecules that absorb microwaves.

In some embodiments, combining the plant material with the microwave absorbing agent comprises combining the plant material with a microwave absorbing composition comprising the microwave absorbing agent, wherein the microwave absorbing composition comprises at least one rod, tube, or sheet as described herein, e.g., and the at least one rod, tube, or sheet comprises the microwave absorbing agent. At least one rod, tube, or sheet may have at least one dimension of about 1 cm to about 100 cm such as about 1 cm to about 10 cm, about 5 cm to about 50 cm, or about 10 cm to about 100 cm. For example, the microwave absorbing composition may comprise at least one sheet, and combining the plant material with the microwave absorbing agent may comprise spreading the plant material on the sheet and rolling the sheet into a coiled sheet.

In some embodiments, the microwave absorbing composition is not a liquid and the microwave absorbing composition does not contain a liquid. In some embodiments, the microwave absorbing composition comprises a solid component and a liquid component. In some embodiments, the microwave absorbing agent is a liquid or gel. In some embodiments, the microwave absorbing agent has a boiling point that is greater than the boiling point of the plant oils targeted for extraction. As one example, the boiling point of the microwave absorbing agent may be greater than 300° F. at atmospheric pressure, greater than 380° F. at atmospheric pressure, or greater than 450° F. at atmospheric pressure.

The microwave absorbing agent is typically a compound other than water. The microwave absorbing agent may be, for example, a compound that is neither present in food nor otherwise found in a typical human diet.

In some embodiments, the plant material consists of less than 20% water by weight such as less than 10% water by weight. The method may further comprise drying the plant material prior to irradiating the microwave absorbing agent.

In some embodiments, the method further comprises altering the propagation direction of the microwave radiation in relation to the microwave absorbing agent to evenly heat the plant material. The propagation direction of the microwave radiation may be altered, for example, by stirring, shaking, or rotating the plant material and the microwave absorbing agent while the microwave absorbing agent is being irradiated.

In preferred embodiments, the method does not cause pyrolysis of the plant oil, volatized oil, condensed oil, or collected oil. In preferred embodiments, the method does not cause pyrolysis of the plant material.

The method may further comprise monitoring at least one temperature inside the extraction chamber, e.g., wherein the at least one temperature inside the extraction chamber includes the temperature of the plant material, the temperature of the microwave absorbing agent, the temperature of any microwave absorbing composition, and/or the temperature of the primed plant material. The method may further comprise maintaining a temperature inside the extraction chamber at about 50° F. to about 450° F. such as about 50° F. to about 100° F., about 50° F. to about 150° F., about 300° F. to about 450° F., 314° F. to about 450° F., about 314° F. to about 427° F., about 314° F. to about 400° F., about 365° F. to about 450° F., about 365° F. to about 427° F., or about 365° F. to about 400° F. Maintaining a temperature inside the extraction chamber may comprise adjusting the power of the microwave radiation, e.g., wherein adjusting the power of the microwave radiation comprises either adjusting the intensity of the microwave radiation that irradiates the microwave absorbing agent and/or cycling the microwave radiation that irradiates the microwave absorbing agent on and off.

In some embodiments, the method further comprises maintaining at least one surface of the cooling chamber at a temperature of about 70° F. to about 314° F. such as about 80° F. to about 314° F., about 100° F. to about 314° F., about 150° F. to about 314° F., about 200° F. to about 314° F., about 212° F. to about 314° F., about 250° F. to about 314° F., about 300° F. to about 314° F., about 80° F. to about 300° F., about 100° F. to about 300° F., about 150° F. to about 300° F., about 200° F. to about 300° F., about 212° F. to about 300° F., about 250° F. to about 300° F., about 80° F. to about 250° F., about 100° F. to about 250° F., about 150° F. to about 250° F., about 200° F. to about 250° F., about 212° F. to about 250° F., about 80° F. to about 200° F., about 100° F. to about 200° F., about 150° F. to about 200° F., about 80° F. to about 150° F., about 100° F. to about 150° F., or about 80° F. to about 100° F. In some embodiments, the method further comprises maintaining at least one surface of the cooling chamber at a temperature of about 35° F. to about 212° F. such as about 40° F. to about 212° F., about 50° F. to about 212° F., about 60° F. to about 212° F., about 70° F. to about 212° F., about 35° F. to about 150° F., about 40° F. to about 150° F., about 50° F. to about 150° F., about 60° F. to about 150° F., about 70° F. to about 150° F., about 35° F. to about 100° F., about 40° F. to about 100° F., about 50° F. to about 100° F., about 60° F. to about 100° F., about 70° F. to about 100° F., about 35° F. to about 90° F., about 40° F. to about 90° F., about 50° F. to about 90° F., about 60° F. to about 90° F., about 70° F. to about 90° F., about 35° F. to about 80° F., about 40° F. to about 80° F., about 50° F. to about 80° F., about 60° F. to about 80° F., about 70° F. to about 80° F., about 35° F. to about 70° F., about 40° F. to about 70° F., about 50° F. to about 70° F., or about 60° F. to about 70° F. (e.g., for terpene recovery).

The method may further comprise removing water from the collected oil. Removing water can be accomplished, for example, by maintaining the collected oil at a temperature of about 212° F. to about 314° F., thereby evaporating water from the collected oil, or by separating an aqueous phase from the collected oil.

In preferred embodiments, the volatized oil, condensed oil, and collected oil lack organic solvent, especially butane and isobutane. In some embodiments, the volatized oil, condensed oil, and collected oil lack chloroform. In some embodiments, the volatized oil, condensed oil, and collected oil lack ethanol.

In some embodiments, inserting the plant material and the microwave absorbing agent into the extraction chamber comprises inserting a cartridge (e.g., removable cartridge) comprising the plant material and the microwave absorbing agent into the extraction chamber.

The extraction chamber may comprise a first opening and a second opening, wherein the plant material and the microwave absorbing agent are inserted into the extraction chamber through the first opening, and the volatized oil in the extraction chamber is directed into the cooling chamber through the second opening.

In some embodiments, the method further comprises sealing the first opening of the extraction chamber prior to irradiating the microwave absorbing agent such that the volatized oil cannot exit the extraction chamber through the first opening.

In some embodiments, the plant material comprises hemp or *Cannabis*. For example, the plant material may comprise *Cannabis sativa, Cannabis indica, Cannabis ruderalis*, a hybridized cross of a species or family of *Cannabis*, or a combination of two or more of the foregoing.

In some embodiments, the volatized oil, condensed oil, and collected oil comprise cannabidiol (CBD), cannabidivarin (CBDV), tetrahydrocannabinol (THC), delta-9-tetrahydrocannabinol, delta-8-tetrahydrocannabinol, tetrahydrocannabivarin (THCV), cannabinol (CBN), cannabigerol, cannabichromene, a chemically converted cannabinoid, any other cannabinoid, linalool, caryophyllene, myrcene, limonene, humulene, pinene, or a combination of two or more of the foregoing. For example, the volatized oil, condensed oil, and collected oil may comprise delta-9-tetrahydrocannabinol. In some embodiments, the volatized oil, condensed oil, and collected oil comprise cannabidiol (CBD). In some embodiments, the collected oil is suitable for use in a pharmaceutical formulation. In some embodiments, the collected oil is suitable for use as a psychotropic substance.

In preferred embodiments, the method does not comprise steam distillation. For example, in some embodiments, the mass of plant oil that is volatized from the plant material is greater than the mass of water that is volatized from the plant material. In some embodiments, the ratio of the mass of plant oil that is volatized from the plant material to the mass of water that is volatized from the plant material is at least about 1:3, about 1:2, about 1:1, about 2:1, or about 3:1.

In some embodiments, the boiling point of the plant oil is greater than 212° F., i.e., the plant oil boils at a temperature greater than 212° F. as it exists in the mixture of the plant material and microwave absorbing agent/composition in the extraction chamber of a system as described herein.

In some embodiments, the invention relates to a method of extracting tetrahydrocannabinol (THC) and/or cannabidiol (CBD) from hemp and/or *Cannabis*, comprising: (1) providing a system for extracting oil from plant material, wherein the system comprises (a) a microwave emitter, (b) an extraction chamber in communication with the microwave emitter such that microwave radiation emitted by the microwave emitter is directed into the extraction chamber, and (c) a cooling chamber in communication with the extraction chamber such that volatized oil in the extraction chamber is directed into the cooling chamber; (2) combining a plant material and a microwave absorbing agent; (3) inserting the plant material and the microwave absorbing agent into the extraction chamber; (4) irradiating the microwave absorbing agent with microwave radiation emitted from the microwave emitter, thereby dielectrically heating the microwave absorbing agent, heating the plant material to a temperature of about 314° F. to about 450° F., and volatizing THC and/or CBD from the plant material to produce a volatized oil comprising the THC and/or CBD; (5) condensing the volatized oil to a temperature of about 70° F. to about 365° in the cooling chamber, thereby producing a condensed oil comprising the THC and/or CBD; and (6) collecting a portion of the condensed oil, thereby producing a collected oil comprising THC and/or CBD that is suitable for human consumption, wherein: the plant material is hemp or *Cannabis*, and the method does not cause pyrolysis of the THC or CBD.

Various aspects of the invention relate to a system for extracting oil from plant material. The system may comprise a microwave emitter; an extraction chamber in communication with the microwave emitter such that microwave radiation emitted by the microwave emitter is directed into the extraction chamber; a microwave absorbing composition disposed in the extraction chamber, wherein the microwave absorbing composition comprises a microwave absorbing agent, and the microwave absorbing composition is not food; a plant material disposed in the extraction chamber; and a cooling chamber in communication with the extraction chamber such that volatized oil in the extraction chamber is directed into the cooling chamber. The system may be configured to dielectrically heat the microwave absorbing agent by microwave radiation emitted from the microwave emitter and to heat the plant material by thermal radiation emitted from the microwave absorbing composition, thereby volatizing oil of the plant material to produce a volatized oil. The cooling chamber may be operable to condense at least a portion of the volatized oil.

The microwave absorbing composition may comprise, for example, a mixture of solids as described herein, e.g., and at least some solids of the mixture of solids may comprise the microwave absorbing agent. The solids of the mixture of solids may be sized, for example, from about 50 µm to about 5 cm such as about 50 µm to about 500 µm, about 100 µm to about 1 mm, about 500 µm to about 5 mm, about 1 mm to about 1 cm, or about 5 mm to about 5 cm. The mixture of solids may be a powder or may comprise beads. The mixture of solids may comprise metal, glass, ceramic, sand, and/or clay.

The microwave absorbing composition may comprise, for example, at least one rod, tube, or sheet as described herein, e.g., wherein the at least one rod, tube, or sheet comprises the microwave absorbing agent. The at least one rod, tube, or sheet may have at least one dimension of about 1 cm to about 100 cm such as about 1 cm to about 10 cm, about 5 cm to about 50 cm, or about 10 cm to about 100 cm. For example, the microwave absorbing composition may comprise at least one sheet, wherein the sheet(s) of the at least one sheet are present as coiled sheet(s).

In some embodiments, the microwave absorbing composition is not a liquid and the microwave absorbing composition does not contain a liquid. In some embodiments, the microwave absorbing composition comprises a solid component and a liquid component. In some embodiments, the microwave absorbing agent is a liquid or gel. In some embodiments, the microwave absorbing agent has a boiling point greater than 360° F. at atmospheric pressure such as greater than 450° F. at atmospheric pressure.

The microwave absorbing agent is typically a compound other than water. The microwave absorbing agent may be, for example, a compound that is neither present in food nor otherwise found in a typical human diet.

In some embodiments, the extraction chamber comprises a first opening shaped and sized to allow the plant material and the microwave absorbing composition to enter and exit the extraction chamber.

The system may further comprise a removable cartridge, wherein the removable cartridge comprises the plant material and the microwave absorbing composition, and the first opening of the extraction chamber is shaped and sized to allow the removable cartridge to enter and exit the extraction chamber. For example, the external walls of the removable cartridge may slidably engage the internal walls of the extraction chamber.

The system may further comprise a sealing puck, wherein the sealing puck seals the first opening thereby inhibiting volatized oil from exiting the extraction chamber through the first opening.

In some embodiments, the extraction chamber comprises a second opening configured to allow the volatized oil to exit the extraction chamber and enter the cooling chamber. In some embodiments, the size of the second opening does not exceed 5 cm in any dimension. For example, the size of the second opening may be less than or equal to 4 cm, 3 cm, 2 cm, 1 cm, or 5 mm.

In some embodiments, the system further comprises a filter, e.g., wherein the filter is positioned between the plant material and the second opening. The filter may be configured both to inhibit the passage of solid particulates from exiting the extraction chamber through the second opening and to allow the passage of the volatized oil through the second opening.

In some embodiments, the extraction chamber comprises a first opening and a second opening; the first opening is shaped and sized to allow the plant material and the microwave absorbing composition to enter and exit the extraction chamber; the first opening is reversibly-sealed, thereby inhibiting volatized oil from exiting the extraction chamber through the first opening; and the second opening is configured to allow volatized oil to exit the extraction chamber and enter the cooling chamber.

In some embodiments, the plant material consists of less than 20% water by weight such as less than 10% water by weight. The system may comprise about 100 g to about 10 kg of plant material such as about 100 g to about 1 kg, about 200 g to about 2 kg, about 300 g to about 3 kg, about 400 g to about 4 kg, or about 500 g to about 5 kg of plant material.

In some embodiments, the plant material comprises hemp or *Cannabis*. For example, the plant material may comprise *Cannabis sativa, Cannabis indica, Cannabis ruderalis*, a hybridized cross of a species or family of *Cannabis*, or a combination of two or more of the foregoing.

In some embodiments, the plant material comprises cannabidiol (CBD), cannabidivarin (CBDV), tetrahydrocannabinol (THC), delta-9-tetrahydrocannabinol, delta-8-tetrahydrocannabinol, tetrahydrocannabivarin (THCV), cannabinol (CBN), cannabigerol, cannabichromene, a chemically converted cannabinoid, any other cannabinoid, linalool, caryophyllene, myrcene, limonene, humulene, pinene, or a combination of two or more of the foregoing. For example, the plant material may comprise tetrahydrocannabinol (THC). In some embodiments, the plant material comprises cannabidiol (CBD).

Various aspects of the invention relate to a system for extracting tetrahydrocannabinol (THC) or cannabidiol (CBD) from hemp or *Cannabis*, comprising: (1) a microwave emitter; (2) an extraction chamber in communication with the microwave emitter such that microwave radiation emitted by the microwave emitter is directed into the extraction chamber; (3) a microwave absorbing composition disposed in the extraction chamber, wherein the microwave absorbing composition is not food, the microwave absorbing composition comprises a microwave absorbing agent, and the microwave absorbing agent has a boiling point that is greater than 360° F. at atmospheric pressure; (4) about 100 g to about 10 kg plant material disposed in the extraction chamber, wherein the plant material is hemp or *Cannabis*, and the plant material comprises THC and/or CBD; and (5) a cooling chamber in communication with the extraction chamber such that volatized THC and/or CBD in the extraction chamber is directed into the cooling chamber, wherein: (6) the extraction chamber comprises a first opening and a second opening; (7) the first opening is shaped and sized to allow the plant material and the microwave absorbing composition to enter and exit the extraction chamber; (8) the first opening is reversibly-sealed, thereby inhibiting volatized THC and/or CBD from exiting the extraction chamber through the first opening; (9) the second opening is configured to allow volatized THC and/or CBD to exit the extraction chamber and enter the cooling chamber; (10) the system is configured to dielectrically heat the microwave absorbing agent by microwave radiation emitted from the microwave emitter; (11) the system is configured to heat the plant material by thermal radiation emitted from the microwave absorbing composition; and (12) the cooling chamber is operable to condense the volatized THC and/or CBD.

BRIEF DESCRIPTION OF THE DRAWINGS

The FIGURE is a diagrammatic view of an embodiment of the present invention.

DETAILED DESCRIPTION OF THE INVENTION

Various embodiments of the invention are based on the finding that the microwaving of a mixture of *Cannabis* and a microwave absorbing agent allows for the efficient extraction on cannabinoids from the *Cannabis*. Such methods may be superior to historical methods of extracting cannabinoids from *Cannabis* because they do not require a solvent such as butane. The systems and methods disclosed herein may also minimize the amount of contact between extracted cannabinoids and moving parts of the systems, which allows for robust systems and minimal maintenance.

The embodiments of the present invention may be differentiated from prior art microwave-based methods of extracting essential oils from plant material because the inventive systems and methods are not systems and methods of steam distillation. Microwave-assisted steam distillation and steam distillation in general has not been proven to be effective in distilling cannabinoids or heavy oleoresins, since the vapor pressure of cannabinoids and heavy oleoresins is extremely low, and thus, cannabinoids and heavy oleoresins are not amenable to prior art methods of microwave-assisted steam distillation. Prior art microwave-based methods of extracting essential oils from plant material rely on the dielectric heating of water to heat the essential oils. The systems and methods disclosed herein rely on the dielectric heating of a microwave absorbing agent, which is typically not water.

A. Plant Material

Various aspects of the invention relate to systems and methods for extracting oil from a plant material.

The plant material is typically not food. The plant material may nevertheless comprise plant oil that is suitable for human consumption. The phrase "suitable for human consumption" refers to therapeutic, medicinal, nutritional, and/or cosmetic use, e.g., as a pharmaceutical agent (such as a psychoactive agent or anticonvulsant) or dietary supplement. Human consumption includes enteral ingestion (e.g., as in a pill, capsule, food, or drink), topical administration, and inhalation (e.g., of vaporized oil). Human consumption requires contacting the plant oil with the body of a human (e.g., in the form of a solid, liquid, or gas). Oil that is not "suitable for human consumption" includes oil that has undergone significant pyrolysis (e.g., greater than 10% of the oil has undergone thermochemical decomposition by weight thereby resulting in greater than 10% weight percent thermochemical decomposition products that are neither terpenes nor cannabinoids) and oil that contains either crude oil, fuel oil, petrochemicals, or non-GRAS solvent (e.g., greater than 0.2% of the oil is crude oil, fuel oil, petrochemicals, and/or non-GRAS solvent by weight).

The plant material may be, for example, hemp or *Cannabis*. The plant material may comprise various forms of tetrahydrocannabinol (THC) and/or various forms of cannabidiol (CBD). In some embodiments, the plant material is essentially free of THC. The plant material may comprise cannabidiol (CBD). The plant material may comprise *Cannabis* such as *Cannabis sativa, Cannabis indica, Cannabis ruderalis*, a hybridized cross of a species or family of *Cannabis*, or a combination of two or more of the foregoing. Other forms of plant material may also be used, e.g., hops.

In some embodiments, the plant material comprises a flower, leaf, and/or stem, e.g., the plant material comprises flowers, leaves, and/or stems. The plant material may consist of greater than 10%, 20%, 25%, 50%, 70%, 75%, 80%, or 90% flowers, such as dried or cured flowers. The plant material may consist of greater than 10%, 20%, 25%, 50%, 70%, 75%, 80%, or 90% pistillate flowers, such as dried or cured pistillate flowers.

In some embodiments, the plant material is dried and/or cured. For example, the plant material may contain less than 20%, 15%, 10%, 9%, 8%, 7%, 6%, or 5% water by weight.

A method may comprise drying the plant material, e.g., before inserting the plant material into an extraction chamber.

The plant material may optionally be ground, e.g., into particles sized between 0.1 μm and 5 mm, 20 μm and 5 mm, or to other grind sizes. In some embodiments, the plant material is not ground, and it is largely intact.

In some embodiments, the plant material does not comprise a fleshy fruit. For example, in some instances, the plant material does not comprise a citrus fruit or a melon. In some embodiments, the plant material is not obtained from a tree. In some embodiments, the plant material does not comprise a fleshy fruit, citrus fruit, citron, shaddock, Tosa shaddock, Sudachi, mandarin orange (*Citrus unshiu*), orange (*Citrus sinensis*), ponkan orange, watermelon, melon, tree, bark, conifer, Japanese cedar (*Cryptomeria japonica*), Japanese cypress (*Chamaecyparis obtusa*), grass, rhizome of ginger, ginger, corn, chaff, rice, rice straw, bagasse, coconut, coconut husk, or livestock excrement.

A system as described herein may comprise at least about 50 grams of plant material such as at least about 75 g, about 100 g, about 150 g, about 200 g, about 250 g, about 300 g, about 400 g, or about 500 g (e.g., within an extraction chamber and/or removable cartridge as described herein). A system as described herein may comprise about 50 grams to 10 kg of plant material such as about 75 g to about 10 kg, about 100 g to about 10 kg, about 150 g to about 10 kg, about 200 g to about 10 kg, about 250 g to about 10 kg, about 300 g to about 10 kg, about 400 g to about 10 kg, about 500 g to about 10 kg, about 50 g to about 5 kg, about 75 g to about 5 kg, about 100 g to about 5 kg, about 150 g to about 5 kg, about 200 g to about 5 kg, about 250 g to about 5 kg, about 300 g to about 5 kg, about 400 g to about 5 kg, about 500 g to about 5 kg, about 10 g to about 1 kg, about 50 g to about 1 kg, about 75 g to about 1 kg, about 100 g to about 1 kg, about 150 g to about 1 kg, about 200 g to about 1 kg, about 250 g to about 1 kg, about 300 g to about 1 kg, about 400 g to about 1 kg, or about 500 g to about 1 kg (e.g., within an extraction chamber and/or removable cartridge as described herein).

A system as described herein may comprise at least about 1 kilograms of plant material such as at least about 2 kg, about 5 kg, about 10 kg, about 25 kg, about 50 kg, about 100 kg, about 250 kg, or about 500 kg (e.g., within an extraction chamber and/or removable cartridge as described herein). A system as described herein may comprise about 2 kg to about 500 kg of plant material such as about 5 kg to about 500 kg, about 10 kg to about 500 kg, about 25 kg to about 500 kg, about 50 kg to about 500 kg, about 100 kg to about 500 kg, about 250 kg to about 500 kg, about 2 kg to about 250 kg, about 5 kg to about 250 kg, about 10 kg to about 250 kg, about 25 kg to about 250 kg, about 50 kg to about 250 kg, about 100 kg to about 250 kg, about 2 kg to about 100 kg, about 5 kg to about 100 kg, about 10 kg to about 100 kg, about 25 kg to about 100 kg, about 50 kg to about 100 kg, about 2 kg to about 50 kg, about 5 kg to about 50 kg, about 10 kg to about 50 kg, about 25 kg to about 50 kg, about 2 kg to about 25 kg, about 5 kg to about 25 kg, about 10 kg to about 25 kg, about 2 kg to about 10 kg, about 5 kg to about 10 kg, or about 2 kg to about 5 kg (e.g., within an extraction chamber and/or removable cartridge as described herein).

B. Plant Oil

A plant oil may comprise various forms of cannabinoids and cannabinoid acids, various forms of cannabidiol (CBD) or cannabidiolic acid (CBDA), cannabidivarin (CBDV), various forms of tetrahydrocannabinol (THC), delta-9-tetrahydrocannabinol, tetrahydrocannabinolic acid, delta-8-tetrahydrocannabinol, tetrahydrocannabivarin (THCV), cannabinol (CBN), cannabigerol, cannabichromene, a chemically converted cannabinoid, any other cannabinoid, linalool, various forms of caryophyllene, myrcene, limonene, humulene, pinene, or a combination of two or more of the foregoing. For example, a volatized oil, condensed oil, and/or collected oil may comprise CBD, e.g., at a concentration of at least about 1%, 5%, 10%, 20%, 25%, 50%, 75%, 80%, or even 90% or higher by weight. Similarly, a volatized oil, condensed oil, and/or collected oil may comprise THC, e.g., at a concentration of at least about 1%, 5%, 10%, 20%, 25%, 50%, 75%, 80%, or even 90% or higher by weight.

The terms "tetrahydrocannabinol" and "THC" refer to (−)-trans-Δ9-tetrahydrocannabinol and isomers thereof.

A volatized oil, condensed oil, and/or collected oil is typically suitable for human consumption, which means that the oil has not undergone significant pyrolysis (e.g., less than 10% of the oil has undergone thermochemical decomposition by weight in which the thermochemical decomposition results in thermochemical decomposition products that are neither terpenes nor cannabinoids) and the oil is essentially free from crude oil, fuel oil, petrochemicals, and non-GRAS solvent (e.g., less than 0.2% of the oil is crude oil, fuel oil, petrochemicals, and/or non-GRAS solvent by weight). A volatized oil, condensed oil, and/or collected oil may comprise less than 10%, 5%, 2%, 1%, 0.5%, 0.2%, 0.1%, 0.05%, 0.02%, or 0.01% oil that has undergone thermochemical decomposition by weight. A volatized oil, condensed oil, and/or collected oil may comprise less than 0.2%, 0.1%, 0.05%, 0.02%, 0.01%, 0.005%, 0.002%, or 0.001% crude oil, fuel oil, petrochemicals, and non-GRAS solvent by weight.

In some embodiments, the boiling point of the plant oil is greater than 212° F., such as greater than about 250° F., about 275° F., or about 300° F. In some embodiments, the boiling point of the plant oil is about 212° F. to about 450° F., about 250° F. to about 450° F., about 275° F. to about 450° F., about 300° F. to about 450° F., about 212° F. to about 400° F., about 250° F. to about 400° F., about 275° F. to about 400° F., or about 300° F. to about 400° F. In some embodiments, the plant oil is immiscible with water and the boiling point of the plant oil is about 212° F. to about 450° F., about 250° F. to about 450° F., about 275° F. to about 450° F., about 300° F. to about 450° F., about 212° F. to about 400° F., about 250° F. to about 400° F., about 275° F. to about 400° F., or about 300° F. to about 400° F. The term boiling point as used herein refers to the boiling point at atmospheric pressure unless the pressure is explicitly specified (e.g., as either a range of pressures or approximate pressures or a specific pressure). The term boiling point as used herein refers to the boiling point of a species as it exists in an extraction chamber in relation to other molecules, i.e., in light of any boiling point elevation (e.g., in the presence of solutes) and any decrease in boiling point (e.g., in the presence of immiscible liquid phases), unless the context of the term boiling point clearly indicates otherwise.

In some embodiments, the volatized oil, condensed oil, and/or collected oil is essentially free of limonene, β-phellandrene, γ-terpinene, β-elemene, α-pinene, β-pinene, linalool, and β-myrcene. In some embodiments, the volatized oil, condensed oil, and/or collected oil is essentially free of THC.

C. Systems

A method may include providing a system for extracting oil from plant material. A system typically comprises (a) a microwave emitter, (b) an extraction chamber in communication with the microwave emitter such that microwave radiation emitted by the microwave emitter is directed into the extraction chamber, and (c) a cooling chamber in communication with the extraction chamber such that volatized oil in the extraction chamber is directed into the cooling chamber.

In some embodiments, an inventive system comprises less than all of the microwave emitter, extraction chamber, and cooling chamber, for example, when the components of the system are supplied separately. An operating version of the inventive system typically comprises a plant material and a microwave absorbing agent as described herein. A system may comprise a plant material, microwave absorbing agent, and/or microwave absorbing composition disposed within the extraction chamber.

D. Microwave Emitter

Microwave emitters are known, and the exact nature of the microwave emitter is not particularly limiting so long as the microwave emitter is capable of dielectrically heating a microwave absorbing agent or heating a microwave absorbing agent by interfacial polarization, which is also known as Maxwell-Wagner-Sillars polarization. A microwave emitter may comprise, for example, a cavity magnetron. A microwave emitter typically emits microwave radiation of a frequency that is capable of dielectrically heating a microwave absorbing agent.

In some embodiments, the microwave emitter is configured to emit microwave radiation at a frequency that favors absorption by the microwave absorbing agent relative to water and/or polysaccharides (e.g., cellulose). In some embodiments, the microwave emitter is configured to emit microwave radiation at a frequency that favors absorption by the microwave absorbing agent relative to the plant material, e.g., to avoid thermal decomposition or combustion of the plant material. The microwave emitter may be a variable frequency microwave emitter. In some embodiments, the system comprises a bandpass filter that favors the transmission of microwave radiation corresponding to frequencies that the microwave absorbing agent can absorb and/or that disfavors the transmission of microwave radiation corresponding to frequencies that water and/or polysaccharides and/or carbon molecules and/or plant materials can absorb.

A system may comprise a waveguide, e.g., to convey microwave radiation from the microwave emitter to the extraction chamber.

A system is typically configured to dynamically alter the power of microwave radiation emitted from the microwave emitter, for example, in response to feedback received from a temperature sensor.

E. Extraction Chamber

An extraction chamber is configured to receive a mixture of plant material and a microwave absorbing agent or microwave absorbing composition. The extraction chamber may be configured to mix, shake, and/or rotate the plant material and microwave absorbing agent or microwave absorbing composition, e.g., thereby allowing homogenous heating.

The extraction chamber typically comprises a first opening and a second opening. The first opening is typically shaped and sized to allow the plant material and a microwave absorbing composition to enter and exit the extraction chamber. The first opening may be shaped and sized to allow a removable cartridge to enter and exit the extraction chamber, e.g., wherein the removable cartridge comprises plant material and a microwave absorbing composition.

A system may comprise a sealing puck, e.g., wherein the sealing puck is configured to seal the first opening thereby inhibiting volatized oil from exiting the extraction chamber through the first opening. The nature of the sealing puck is not particularly limiting so long as the sealing puck is stable at temperatures up to at least 400° F., stable both in water and in plant oil, and stable when exposed to microwave radiation. The sealing puck may optionally be opaque to microwave radiation.

A first opening may be reversibly-sealed (e.g., with a sealing puck), thereby inhibiting volatized oil from exiting the extraction chamber through the first opening.

The second opening is typically configured to allow volatized oil to exit the extraction chamber and enter the cooling chamber. In some embodiments, the second opening does not exceed 5 cm in any dimension. For example, the second opening may not exceed either 4 cm, 3 cm, 2 cm, 1 cm, or 5 mm in any dimension. The second opening may be circular or substantially circular, although the precise geometry of the second opening is not particularly limiting. A system may comprise a filter positioned within or adjacent to the second opening and configured to inhibit the passage of solid particles through the second opening. A filter is typically configured to inhibit the passage of solid particulates from exiting the extraction chamber through the second opening. A filter is typically configured to allow the passage of the volatized oil through the second opening. A filter may optionally be heated, e.g., to a temperature greater than about 200° F., 300° F., 320° F., 350° F., 360° F., 370° F., 380° F., or 400° F. In some embodiments, the filter may comprise or consist of a microwave absorbing fiber or sintered material to ensure that the filter is sufficiently heated to inhibit condensation of the volatized oils either onto the filter or adjacent to the filter.

A system may optionally comprise a membrane positioned within or adjacent to the second opening and configured to inhibit the passage of liquids through the second opening. A membrane is typically configured to inhibit the passage of liquid from exiting the extraction chamber through the second opening. A membrane is typically configured to allow the passage of the volatized oil through the second opening.

In some embodiments, the first opening is positioned at the top of the extraction chamber and the second opening is positioned at the bottom of the extraction chamber, e.g., such that a removable cartridge may be inserted into the extraction chamber through the first opening and volatized oil may be directed from the extraction chamber into the cooling chamber through the second opening. Such configurations, one of which is illustrated in the FIGURE, are suitable, for example, when the plant material and microwave absorbing composition/agent are substantially solid during loading and heating.

In embodiments in which the plant material and/or microwave absorbing composition/agent comprises a liquid, the system may include a second opening positioned either on a side or on the top of the extraction chamber and/or a membrane that covers the second opening to inhibit the flow of the liquid through the second opening. The precise locations of the first opening and second opening are not particularly limiting, however, as one of ordinary skill readily knows to position the first opening and second opening and to otherwise configure the system for ease of use and maintenance.

The extraction chamber is typically not significantly pressurized, e.g., because volatized oil and other gases may escape the extraction chamber to enter the cooling chamber. The method may include maintaining the pressure of the extraction chamber at about 0.3 atmospheres to about 5 atmospheres, such as about 0.5 atm to about 2 atm, about 0.6 atm to about 1.8 atm, or about 0.8 atm to about 1.6 atm. The ambient pressure of urbanized regions of the United States, for example, ranges from about 0.8 atm (e.g., in Denver, Colorado) to about 1.0 atm (e.g., in Miami, Florida), and the microwave-assisted volatilization of plant oil may increase the pressure of a system significantly higher than ambient pressure. The system may nevertheless be configured to maintain a pressure close to ambient pressure in the extraction chamber because higher pressures increase the boiling point of the plant oil.

Those of skill in the art will immediately recognize that the assistance of a vacuum may increase the rate of vaporization and/or allow for the reduction of temperatures required to volatilize oils from plant material. In some embodiments, a method comprises applying a vacuum to the extraction chamber and/or any removable cartridge. A system may comprise a vacuum pump, e.g., wherein the vacuum pump is operable to reduce the pressure in the extraction chamber and/or any removable cartridge. The vacuum may reduce the pressure in the extraction chamber and/or any removable cartridge to about 0.05 atm to about 1 atm, such as about 0.1 atm to about 1 atm, about 0.2 atm to about 1 atm, about 0.5 atm to about 1 atm, about 0.05 atm to about 0.8 atm, about 0.1 atm to about 0.8 atm, about 0.2 atm to about 0.8 atm, about 0.5 atm to about 0.8 atm, about 0.05 atm to about 0.6 atm, about 0.1 atm to about 0.6 atm, about 0.2 atm to about 0.6 atm, about 0.5 atm to about 0.6 atm, about 0.05 atm to about 0.5 atm, about 0.1 atm to about 0.5 atm, or about 0.2 atm to about 0.5 atm.

F. Cooling Chamber

In certain embodiments, the system includes a cooling chamber in communication with the extraction chamber such that volatized oil is directed into the cooling chamber. The cooling chamber is typically operable to cool the volatized oil to or below a condensation temperature of the oil such that at least some of the volatized oil liquefies.

The nature of the cooling chamber is not particularly limiting. The cooling chamber may comprise a condenser such as a Liebig condenser, West condenser, Allihn condenser, Davies condenser, Graham condenser, Friedrichs condenser, spiral condenser, coil condenser, or Dimroth condenser. A condenser may be cooled, for example, with water.

In some embodiments, the cooling chamber lacks a condenser, e.g., because volatized oil may condense at a temperature that is substantially greater than room temperature.

A cooling chamber may comprise one or more heated surfaces, e.g., wherein the "heated" surface(s) are heated relative to ambient temperature (i.e., 70° F.).

Surfaces of the cooling chamber may be maintained at a temperature of about 70° F. to about 350° F., such as about 70° F. to about 314° F., about 70° F. to about 300° F., about 70° F. to about 250° F., about 70° F. to about 212° F., about 70° F. to about 200° F., about 70° F. to about 150° F., about 70° F. to about 100° F., about 100° F. to about 350° F., about 100° F. to about 314° F., about 100° F. to about 300° F., about 100° F. to about 250° F., about 100° F. to about 212° F., about 100° F. to about 200° F., about 100° F. to about 150° F., about 150° F. to about 350° F., about 150° F. to about 314° F., about 150° F. to about 300° F., about 150° F. to about 250° F., about 150° F. to about 212° F., about 150° F. to about 200° F., about 200° F. to about 350° F., about 200° F. to about 314° F., about 200° F. to about 300° F., about 200° F. to about 250° F., about 200° F. to about 212° F., about 212° F. to about 350° F., about 212° F. to about 314° F., about 212° F. to about 300° F., about 212° F. to about 250° F., about 250° F. to about 350° F., about 250° F. to about 314° F., or about 250° F. to about 300° F. In some embodiments, at least one surface of the cooling chamber is maintained at a temperature of about −325° F. to about 300° F. such as about −325° F. to about −250° F., about −300° F. to about −200° F., about −250° F. to about −150° F., about −200° F. to about −100° F., about −150° F. to about −50° F., about −100° F. to about 0° F., about −50° F. to about 50° F., about 0° F. to about 100° F., or about 50° F. to about 150° F. In some embodiments, for example, the surfaces of the cooling chamber are maintained at a temperature of about 212° F. to about 314° F., thereby allowing the condensation of cannabinoids and inhibiting the condensation of water.

In some embodiments the temperature of the cooling chamber is maintained at a temperature low enough to condense the volatilized oil, but high enough to keep the condensed oil in a liquid state so it readily flows from the cooling chamber. In some embodiments, the cooling chamber may be kept at a very cold temperature to capture all forms of volatilized oils, and then be periodically heated to expel the collected oil.

In some embodiments, the cooling chamber may be cooled to lower temperatures, such as below 100° F., below 90° F., below 80° F., below 70° F., or below 50° F., 30° F., 20° F., 0° F. or lower. Using lower temperatures in the cooling chamber may facilitate the collection of lower boiling point terpenes or volatile oils. Using lower temperatures in the cooling chamber may also be required in embodiments where a vacuum is used to assist the distillation of the extracted oils from the plant materials. In other embodiments, the cooling chamber may be cooled to a range of about 50° F. to about 30° F., about 30° F. to about 10° F., about 10° F. to about −10° F., about −10° F. to about −30° F., about 50° F. to about 0° F., about 30° F. to about −100° F., about 0° F. to about −200° F., about −50° F. to about −325° F., or other low temperatures that will be generally known to those skilled in the art of distillation.

The cooling chamber may be a spray cooling chamber having a pressurized sprayer operable to spray collection solvent into the volatized oil such that the collection solvent rapidly cools the volatized oil to or below a condensation temperature of the volatized oil. Spray cooling chambers are described, for example, in PCT Patent Application Publication No. WO2015049585 and WO2016161420, each of which is hereby incorporated by reference. The sprayed collection solvent may optionally be recirculated such that the collection solvent comprises condensed oil from the liquid collector, and the system may further include a pump operable to pump the collection solvent and extracted oil from the liquid collector to the high pressure sprayer. Alternatively, the sprayed collection solvent is a substantially purified collection solvent. A collection solvent cooler may be provided to cool the collection solvent for the high pressure sprayer. A collection solvent preferably consists essentially of GRAS solvents such as ethanol and water (e.g., and possibly solutes such as trace solutes).

G. Microwave Absorbing Agent

A system may comprise a microwave absorbing agent, e.g., wherein the microwave absorbing agent is disposed in the extraction chamber of the system. A method may comprise combining a plant material with a microwave absorbing agent.

In certain embodiments, the microwave absorbing agent is neither present in food nor otherwise found in a typical human diet.

In some embodiments, the microwave absorbing agent is present in food, plant material, or another type of composition that is exposed to microwaves and yet the amount of the microwave absorbing agent used in the system and methods described herein is greater than the amount of the microwave absorbing agent as it is typically found in the food, plant material, or other type of composition.

A system may comprise at least 1 gram of the microwave absorbing agent such as at least about 2 g, about 3 g, about 4 g, about 5 g, about 6 g, about 7 g, about 8 g, about 9 g, about 10 g, about 15 g, about 20 g, about 25 g, about 30 g, about 40 g, about 50 g, about 75 g, about 100 g, about 150 g, about 200 g, about 250 g, about 300 g, about 400 g, or about 500 g. A system may comprise 1 g to about 10 kg of the microwave absorbing agent such as about 10 g to about 10 kg, about 15 g to about 10 kg, about 20 g to about 10 kg, about 25 g to about 10 kg, about 30 g to about 10 kg, about 40 g to about 10 kg, about 50 g to about 10 kg, about 75 g to about 10 kg, about 100 g to about 10 kg, about 150 g to about 10 kg, about 200 g to about 10 kg, about 250 g to about 10 kg, about 300 g to about 10 kg, about 400 g to about 10 kg, about 500 g to about 10 kg, about 10 g to about 5 kg, about 15 g to about 5 kg, about 20 g to about 5 kg, about 25 g to about 5 kg, about 30 g to about 5 kg, about 40 g to about 5 kg, about 50 g to about 5 kg, about 75 g to about 5 kg, about 100 g to about 5 kg, about 150 g to about 5 kg, about 200 g to about 5 kg, about 250 g to about 5 kg, about 300 g to about 5 kg, about 400 g to about 5 kg, about 500 g to about 5 kg, about 10 g to about 1 kg, about 15 g to about 1 kg, about 20 g to about 1 kg, about 25 g to about 1 kg, about 30 g to about 1 kg, about 40 g to about 1 kg, about 50 g to about 1 kg, about 75 g to about 1 kg, about 100 g to about 1 kg, about 150 g to about 1 kg, about 200 g to about 1 kg, about 250 g to about 1 kg, about 300 g to about 1 kg, about 400 g to about 1 kg, or about 500 g to about 1 kg.

A system may comprise at least 1 kilogram of the microwave absorbing agent such as at least about 2 kg, about 3 kg, about 4 kg, about 5 kg, about 6 kg, about 7 kg, about 8 kg, about 9 kg, about 10 kg, about 15 kg, about 20 kg, about 25 kg, about 30 kg, about 40 kg, about 50 kg, about 75 kg, about 100 kg, about 150 kg, about 200 kg, about 250 kg, about 300 kg, about 400 kg, or about 500 kg. A system may comprise 1 kg to about 500 kg of the microwave absorbing agent such as about 10 kg to about 500 kg, about 15 kg to about 500 kg, about 20 kg to about 500 kg, about 25 kg to about 500 kg, about 30 kg to about 500 kg, about 40 kg to about 500 kg, about 50 kg to about 500 kg, about 75 kg to about 500 kg, about 100 kg to about 500 kg, about 150 kg to about 500 kg, about 200 kg to about 500 kg, about 250 kg to about 500 kg, about 300 kg to about 500 kg, about 400 kg to about 500 kg, about 1 kg to about 100 kg, about 5 kg to about 100 kg, about 10 kg to about 100 kg, about 15 kg to about 100 kg, about 20 kg to about 100 kg, about 25 kg to about 100 kg, about 30 kg to about 100 kg, about 40 kg to about 100 kg, about 50 kg to about 100 kg, about 75 kg to about 100 kg, about 1 kg to about 50 kg, about 5 kg to about 50 kg, about 10 kg to about 50 kg, about 15 kg to about 50 kg, about 20 kg to about 50 kg, about 25 kg to about 50 kg, about 30 kg to about 50 kg, about 40 kg to about 50 kg, about 1 kg to about 10 kg, about 5 kg to about 20 kg, about 10 kg to about 20 kg, or about 15 kg to about 20 kg.

A system may comprise a microwave absorbing agent and a plant material at a ratio (mass:mass) of about 10:1 to about 1:100 such as about 10:1 to about 5:1, about 10:1 to about 1:1, about 5:1 to about 1:1, about 5:1 to about 1:2, about 2:1 to about 1:1, about 2:1 to about 1:2, about 1:1 to about 1:2, about 1:1 to about 1:3, about 1:1 to about 1:4, about 1:1 to about 1:5, about 1:1 to about 1:10, about 1:1 to about 1:20, about 3:2 to about 2:3, about 3:2 to about 1:1, about 3:2 to about 1:3, about 2:3 to about 1:3, about 2:3 to about 1:1, about 1:2 to about 1:3, about 1:2 to about 1:4, about 1:2 to about 1:5, about 1:3 to about 1:4, about 1:3 to about 1:5, about 1:3 to about 1:10, about 1:4 to about 1:5, about 1:4 to about 1:10, about 1:5 to about 1:10, about 1:5 to about 1:20, about 1:5 to about 1:25, about 1:10 to about 1:20, about 1:10 to about 1:50, about 1:10 to about 1:100, about 1:20 to about 1:100, or about 1:50 to about 1:100, e.g., about 10:1, 5:1, 4:1, 3:1, 2:1, 3:2, 4:3, 5:4, 1:1, 4:5, 3:4, 2:3, 1:2, 1:3, 1:4, 1:5, 1:6, 1:7, 1:8, 1:9, 1:10, 1:20, 1:25, 1:30, 1:40, 1:50, or 1:100.

A method may comprise combining a plant material and a microwave absorbing agent, inserting the plant material and the microwave absorbing agent into an extraction chamber, irradiating the microwave absorbing agent, and/or dielectrically heating the microwave absorbing agent, wherein the amount of the microwave absorbing agent is at least 1 kilogram of the microwave absorbing agent such as at least about 2 kg, about 3 kg, about 4 kg, about 5 kg, about 6 kg, about 7 kg, about 8 kg, about 9 kg, about 10 kg, about 15 kg, about 20 kg, about 25 kg, about 30 kg, about 40 kg, about 50 kg, about 75 kg, about 100 kg, about 150 kg, about 200 kg, about 250 kg, about 300 kg, about 400 kg, or about 500 kg. A method may comprise combining a plant material and a microwave absorbing agent, inserting the plant material and the microwave absorbing agent into an extraction chamber, irradiating the microwave absorbing agent, and/or dielectrically heating the microwave absorbing agent, wherein the amount of the microwave absorbing agent is 1 g to about 10 kg such as about 10 g to about 10 kg, about 15 g to about 10 kg, about 20 g to about 10 kg, about 25 g to about 10 kg, about 30 g to about 10 kg, about 40 g to about 10 kg, about 50 g to about 10 kg, about 75 g to about 10 kg, about 100 g to about 10 kg, about 150 g to about 10 kg, about 200 g to about 10 kg, about 250 g to about 10 kg, about 300 g to about 10 kg, about 400 g to about 10 kg, about 500 g to about 10 kg, about 10 g to about 5 kg, about 15 g to about 5 kg, about 20 g to about 5 kg, about 25 g to about 5 kg, about 30 g to about 5 kg, about 40 g to about 5 kg, about 50 g to about 5 kg, about 75 g to about 5 kg, about 100 g to about 5 kg, about 150 g to about 5 kg, about 200 g to about 5 kg, about 250 g to about 5 kg, about 300 g to about 5 kg, about 400 g to about 5 kg, about 500 g to about 5 kg, about 10 g to about 1 kg, about 15 g to about 1 kg, about 20 g to about 1 kg, about 25 g to about 1 kg, about 30 g to about 1 kg, about 40 g to about 1 kg, about 50 g to about 1 kg, about 75 g to about 1 kg, about 100 g to about 1 kg, about 150 g to about 1 kg, about 200 g to about 1 kg, about 250 g to about 1 kg, about 300 g to about 1 kg, about 400 g to about 1 kg, or about 500 g to about 1 kg.

A method may comprise combining a plant material and a microwave absorbing agent, inserting the plant material and the microwave absorbing agent into an extraction chamber, irradiating the microwave absorbing agent, and/or dielectrically heating the microwave absorbing agent, wherein the amount of the microwave absorbing agent is at least 1 gram such as at least about 2 g, about 3 g, about 4 g, about 5 g, about 6 g, about 7 g, about 8 g, about 9 g, about 10 g, about 15 g, about 20 g, about 25 g, about 30 g, about 40 g, about 50 g, about 75 g, about 100 g, about 150 g, about 200 g, about 250 g, about 300 g, about 400 g, or about 500 g. A method may comprise combining a plant material and a microwave absorbing agent, inserting the plant material and the microwave absorbing agent into an extraction chamber, irradiating the microwave absorbing agent, and/or dielectrically heating the microwave absorbing agent, wherein the amount of the microwave absorbing agent is 1 kg to about 500 kg such as about 10 kg to about 500 kg, about 15 kg to about 500 kg, about 20 kg to about 500 kg, about 25 kg to about 500 kg, about 30 kg to about 500 kg, about 40 kg to about 500 kg, about 50 kg to about 500 kg, about 75 kg to about 500 kg, about 100 kg to about 500 kg, about 150 kg to about 500 kg, about 200 kg to about 500 kg, about 250 kg to about 500 kg, about 300 kg to about 500 kg, about 400 kg to about 500 kg, about 1 kg to about 100 kg, about 5 kg to about 100 kg, about 10 kg to about 100 kg, about 15 kg to about 100 kg, about 20 kg to about 100 kg, about 25 kg to about 100 kg, about 30 kg to about 100 kg, about 40 kg to about 100 kg, about 50 kg to about 100 kg, about 75 kg to about 100 kg, about 1 kg to about 50 kg, about 5 kg to about 50 kg, about 10 kg to about 50 kg, about 15 kg to about 50 kg, about 20 kg to about 50 kg, about 25 kg to about 50 kg, about 30 kg to about 50 kg, about 40 kg to about 50 kg, about 1 kg to about 10 kg, about 5 kg to about 20 kg, about 10 kg to about 20 kg, or about 15 kg to about 20 kg.

A method may comprise combining a microwave absorbing agent and a plant material at a ratio (mass:mass) of about 10:1 to about 1:100 such as about 10:1 to about 5:1, about 10:1 to about 1:1, about 5:1 to about 1:1, about 5:1 to about 1:2, about 2:1 to about 1:1, about 2:1 to about 1:2, about 1:1 to about 1:2, about 1:1 to about 1:3, about 1:1 to about 1:4, about 1:1 to about 1:5, about 1:1 to about 1:10, about 1:1 to about 1:20, about 3:2 to about 2:3, about 3:2 to about 1:1, about 3:2 to about 1:3, about 2:3 to about 1:3, about 2:3 to about 1:1, about 1:2 to about 1:3, about 1:2 to about 1:4, about 1:2 to about 1:5, about 1:3 to about 1:4, about 1:3 to about 1:5, about 1:3 to about 1:10, about 1:4 to about 1:5, about 1:4 to about 1:10, about 1:5 to about 1:10, about 1:5 to about 1:20, about 1:5 to about 1:25, about 1:10 to about 1:20, about 1:10 to about 1:50, about 1:10 to about 1:100, about 1:20 to about 1:100, or about 1:50 to about 1:100, e.g., about 10:1, 5:1, 4:1, 3:1, 2:1, 3:2, 4:3, 5:4, 1:1, 4:5, 3:4, 2:3, 1:2, 1:3, 1:4, 1:5, 1:6, 1:7, 1:8, 1:9, 1:10, 1:20, 1:25, 1:30, 1:40, 1:50, or 1:100.

Polar compounds absorb microwaves including both organic and inorganic polar compounds. Inorganic ionic molecules may be preferable for use as microwave absorbing agents because inorganic molecules display high thermo-stability relative to organic molecules and because ions are generally less volatile than uncharged molecules. Examples of inexpensive inorganic ionic molecules include phosphates, carbonates, nitrates, sulfates, and silicates. A microwave absorbing agent may be a phosphate, carbonate, nitrate, sulfate, or silicate. Phosphoric acid, for example, has a boiling point of 415° F., and thus, phosphates are suitable as microwave absorbing agents for volatizing plant oils having boiling points less than 415° F. Examples of inexpensive polar organic molecules include starches, sugars, fatty acids, amines, various types of carbon containing molecules, and glycol ethers. A microwave absorbing agent may be a starch, sugar, fatty acid, amine, another type of carbon-containing molecule, or glycol ether. Lauric acid and stearic acid, for example, have boiling points of 568° F. and 682° F., respectively, and thus, lauric acid (and/or laurate ion) and stearic acid (and/or stearate ion) are generally suitable for use as microwave absorbing agents. Glycerol has a boiling point of 554° F., and thus, glycerol is generally suitable for use as a microwave absorbing agent. Ethylene glycol has a boiling point of 387° F., and thus, ethylene glycol is suitable as a microwave absorbing agent for volatizing plant oils having boiling points less than 387° F. Saturated fatty acids and plant oils with high smoke points, especially hydrogenated plant oils, are generally useful as microwave absorbing agents (e.g., coconut oil, cottonseed oil, and palm oil). In some embodiments, the microwave absorbing agent is a polymer, such as polyethylene glycol or polysiloxane. The microwave-absorbing agent may be a carbon-based solid such as activated carbon, char, amorphous carbon, a graphite intercalation compound, a carbon nanotube, or exfoliated graphite, e.g., wherein microwave irradiation of the microwave-absorbing agent causes interfacial polarization (Maxwell-Wagner-Sillars polarization). The microwave absorbing agent is typically not water.

A microwave absorbing agent typically has a boiling point that is greater than the boiling point of the plant oil. For example, a microwave absorbing agent may have a boiling point greater than about 300° F., about 310° F., about 314° F., about 320° F., about 330° F., about 340° F., about 350° F., about 360° F., about 370° F., about 380° F., about 390° F., about 400° F., about 410° F., about 420° F., about 430° F., about 440° F., or about 450° F. The precise boiling point of the microwave absorbing agent is not particularly limiting so long as it is greater than the boiling point of the plant oil. The boiling point of water in comparison is 212° F.

A microwave absorbing agent typically has an autoignition temperature that is greater than the boiling point of the plant oil. For example, a microwave absorbing agent may have an autoignition temperature greater than about 360° F., about 370° F., about 380° F., about 390° F., about 400° F., about 410° F., about 420° F., about 430° F., about 440° F., or about 450° F. The precise autoignition temperature of the microwave absorbing agent is not particularly limiting so long as it is greater than the boiling point of the plant oil.

H. Microwave Absorbing Composition

A system optionally comprises a microwave absorbing composition, e.g., wherein the microwave absorbing composition is disposed in the extraction chamber of the system. A microwave absorbing composition comprises a microwave absorbing agent as the term "microwave absorbing composition" is used herein. A method may comprise combining a plant material with a microwave absorbing composition. A microwave absorbing composition is typically a solid or a solid that has been wetted with a liquid.

A microwave absorbing composition typically has a high surface-area-to-volume ratio, e.g., at least about 100 $m^2$ to 1 $m^3$, 200 $m^2$ to 1 $m^3$, 500 $m^2$ to 1 $m^3$, 1000 $m^2$ to 1 $m^3$, 10,000 $m^2$ to 1 $m^3$, 100,000 $m^2$ to 1 $m^3$, or 1,000,000 $m^2$ to 1 $m^3$. A spherical 10 μm particle, for example, has a surface-area-to-volume ratio of 600,000 $m^2$ to 1 $m^3$ and a spherical 5 cm bead has a surface-area-to-volume ratio of 120 $m^2$ to 1 $m^3$. A high surface-area-to-volume ratio allows for efficient thermal conduction between the microwave absorbing composition and a plant material.

A microwave absorbing composition may comprise a mixture of solids that are sized from about 0.1 μm to about 250 μm, about 0.1 μm to about 500 μm, about 0.1 μm to about 1 mm, about 1 μm to about 250 μm, about 1 μm to about 500 μm, about 1 μm to about 1 mm, about 10 μm to about 250 μm, about 10 μm to about 500 μm, about 10 μm to about 1 mm, about 50 μm to about 500 μm, about 100 μm to about 1 mm, about 500 μm to about 5 mm, about 1 mm to about 1 cm, or about 5 mm to about 5 cm. The mixture of solids may comprise, for example, a powder and/or beads, fibers of the various diameters described, grits, flakes, structured packing and/or other mixtures of solids that promote a high surface area.

In some embodiments, a microwave absorbing composition may consist of a generally non-microwave absorbing or weak microwave absorbing substrate that has been impregnated with one or more microwave absorbing agents. Such impregnated substrates may contain various types of polar molecules, dipole molecules, various types of carbon molecules, carbonates, any of the microwave absorbing agents specifically mentioned in this application, or even encapsulated water molecules or mixtures of such. Impregnated glass substrates, impregnated ceramic substrates, impregnated clays, impregnated salts, impregnated metals or other impregnated substrates may be used as a microwave absorbing composition. Some non-limiting examples of generally non-microwave absorbing substrates that may be impregnated with one or more microwave absorbing agents include various forms of glass beads, glass powders, glass grits, glass fibers, glass packing, glass wools, and other forms of glass that contain microwave absorbing agents such as ions, dipole molecules, polar molecules, and/or other microwave absorbing impurities, various forms of ceramic beads, ceramic powders, and ceramic grits or ceramic flakes that contain microwave absorbing agents such as ions, impregnated water molecules, dipole molecules, polar molecules, and/or other microwave absorbing substances, various forms of clays that contain specific microwave absorbing agents, and other substrates containing microwave absorbing agents that will be generally known to those of skill in the art. An additional example of an impregnated substrate is sand, or various forms of crushed rocks or minerals. Various types of carbonate minerals may also be used.

The mixture of solids may comprise various types of metals, glass, ceramics, sand, and/or clays. In some embodiments, the microwave absorbing composition is not a liquid. In some embodiments, the microwave absorbing composition does not contain a liquid. Alternatively, the microwave absorbing composition may comprise a solid component and a liquid component, e.g., wherein the solid component encapsulates the liquid component to inhibit the release of the liquid component from the microwave absorbing composition, or wherein the liquid component coats the composition in such a way that the liquid remains on the surface of the solid. Still in other embodiments, the microwave absorbing composition is a liquid or gel.

A microwave absorbing composition may comprise at least one rod, tube, or sheet. The at least one rod, tube, or sheet may have at least one dimension of about 1 cm to about 100 cm such as about 1 cm to about 10 cm, about 5 cm to about 50 cm, or about 10 cm to about 100 cm. For example, a rod may have (1) a diameter of about 50 µm to about 5 cm, about 50 µm to about 500 µm, about 100 µm to about 1 mm, about 500 µm to about 5 mm, about 1 mm to about 1 cm, or about 5 mm to about 5 cm and (2) a length of about 1 cm to about 1 m, about 1 cm to about 10 cm, about 5 cm to about 50 cm, about 10 cm to about 100 cm, about 50 cm to about 500 cm, or about 100 cm to about 1 m. A tube may have (1) an internal diameter of about 50 µm to about 5 cm, about 50 µm to about 500 µm, about 100 µm to about 1 mm, about 500 µm to about 5 mm, about 1 mm to about 1 cm, or about 5 mm to about 5 cm, (2) a length of about 1 cm to about 1 m, about 1 cm to about 10 cm, about 5 cm to about 50 cm, about 10 cm to about 100 cm, about 50 cm to about 500 cm, or about 100 cm to about 1 m, and (3) a thickness of about 50 µm to about 1 cm, about 50 µm to about 500 µm, about 100 µm to about 1 mm, about 500 µm to about 5 mm, or about 1 mm to about 1 cm. A sheet may have (1) a length and/or width of about 1 cm to about 1 m, about 1 cm to about 10 cm, about 5 cm to about 50 cm, about 10 cm to about 100 cm, about 50 cm to about 500 cm, or about 100 cm to about 1 m, and (2) a thickness of about 10 µm to about 1 cm, about 10 µm to about 100 µm, about 50 µm to about 500 µm, about 100 µm to about 1 mm, about 500 µm to about 5 mm, or about 1 mm to about 1 cm.

A method may comprise combining a plant material with a microwave absorbing agent, wherein a microwave absorbing composition comprises the microwave absorbing agent, the microwave absorbing composition is a sheet, and combining comprises spreading the plant material on the sheet and rolling the sheet into a coiled sheet.

In certain embodiments, the microwave absorbing composition is neither present in food nor otherwise found in a typical human diet.

In some embodiments, the microwave absorbing composition is present in food, plant material, or another type of composition that is exposed to microwaves and yet the amount of the microwave absorbing composition used in the system and methods described herein is greater than the amount of the microwave absorbing composition as it is found in the food, plant material, or other type of composition.

A system may comprise at least 1 gram of the microwave absorbing composition such as at least about 2 g, about 3 g, about 4 g, about 5 g, about 6 g, about 7 g, about 8 g, about 9 g, about 10 g, about 15 g, about 20 g, about 25 g, about 30 g, about 40 g, about 50 g, about 75 g, about 100 g, about 150 g, about 200 g, about 250 g, about 300 g, about 400 g, or about 500 g. A system may comprise 1 g to about 10 kg of the microwave absorbing composition such as about 10 g to about 10 kg, about 15 g to about 10 kg, about 20 g to about 10 kg, about 25 g to about 10 kg, about 30 g to about 10 kg, about 40 g to about 10 kg, about 50 g to about 10 kg, about 75 g to about 10 kg, about 100 g to about 10 kg, about 150 g to about 10 kg, about 200 g to about 10 kg, about 250 g to about 10 kg, about 300 g to about 10 kg, about 400 g to about 10 kg, about 500 g to about 10 kg, about 10 g to about 5 kg, about 15 g to about 5 kg, about 20 g to about 5 kg, about 25 g to about 5 kg, about 30 g to about 5 kg, about 40 g to about 5 kg, about 50 g to about 5 kg, about 75 g to about 5 kg, about 100 g to about 5 kg, about 150 g to about 5 kg, about 200 g to about 5 kg, about 250 g to about 5 kg, about 300 g to about 5 kg, about 400 g to about 5 kg, about 500 g to about 5 kg, about 10 g to about 1 kg, about 15 g to about 1 kg, about 20 g to about 1 kg, about 25 g to about 1 kg, about 30 g to about 1 kg, about 40 g to about 1 kg, about 50 g to about 1 kg, about 75 g to about 1 kg, about 100 g to about 1 kg, about 150 g to about 1 kg, about 200 g to about 1 kg, about 250 g to about 1 kg, about 300 g to about 1 kg, about 400 g to about 1 kg, or about 500 g to about 1 kg.

A system may comprise a microwave absorbing composition and a plant material at a ratio (mass:mass) of about 10:1 to about 1:100 such as about 10:1 to about 5:1, about 10:1 to about 1:1, about 5:1 to about 1:1, about 5:1 to about 1:2, about 2:1 to about 1:1, about 2:1 to about 1:2, about 1:1 to about 1:2, about 1:1 to about 1:3, about 1:1 to about 1:4, about 1:1 to about 1:5, about 1:1 to about 1:10, about 1:1 to about 1:20, about 3:2 to about 2:3, about 3:2 to about 1:1, about 3:2 to about 1:3, about 2:3 to about 1:3, about 2:3 to about 1:1, about 1:2 to about 1:3, about 1:2 to about 1:4, about 1:2 to about 1:5, about 1:3 to about 1:4, about 1:3 to about 1:5, about 1:3 to about 1:10, about 1:4 to about 1:5, about 1:4 to about 1:10, about 1:5 to about 1:10, about 1:5 to about 1:20, about 1:5 to about 1:25, about 1:10 to about 1:20, about 1:10 to about 1:50, about 1:10 to about 1:100, about 1:20 to about 1:100, or about 1:50 to about 1:100, e.g., about 10:1, 5:1, 4:1, 3:1, 2:1, 3:2, 4:3, 5:4, 1:1, 4:5, 3:4, 2:3, 1:2, 1:3, 1:4, 1:5, 1:6, 1:7, 1:8, 1:9, 1:10, 1:20, 1:25, 1:30, 1:40, 1:50, or 1:100.

A method may comprise combining a plant material and a microwave absorbing composition, inserting the plant material and the microwave absorbing composition into an extraction chamber, irradiating the microwave absorbing composition, and/or dielectrically heating the microwave absorbing composition, wherein the amount of the microwave absorbing composition is at least 1 gram such as at least about 2 g, about 3 g, about 4 g, about 5 g, about 6 g, about 7 g, about 8 g, about 9 g, about 10 g, about 15 g, about 20 g, about 25 g, about 30 g, about 40 g, about 50 g, about 75 g, about 100 g, about 150 g, about 200 g, about 250 g, about 300 g, about 400 g, or about 500 g. A method may comprise combining a plant material and a microwave absorbing composition, inserting the plant material and the microwave absorbing composition into an extraction chamber, irradiating the microwave absorbing composition, and/or dielectrically heating the microwave absorbing composition, wherein the amount of the microwave absorbing composition is 1 g to about 10 kg such as about 10 g to about 10 kg, about 15 g to about 10 kg, about 20 g to about 10 kg, about 25 g to about 10 kg, about 30 g to about 10 kg, about 40 g to about 10 kg, about 50 g to about 10 kg, about 75 g to about 10 kg, about 100 g to about 10 kg, about 150 g to about 10 kg, about 200 g to about 10 kg, about 250 g to about 10 kg, about 300 g to about 10 kg, about 400 g to about 10 kg, about 500 g to about 10 kg, about 10 g to about 5 kg, about 15 g to about 5 kg, about 20 g to about 5 kg, about 25 g to about 5 kg, about 30 g to about 5 kg, about 40 g to about 5 kg, about 50 g to about 5 kg, about 75 g to about 5 kg, about 100 g to about 5 kg, about 150 g to about 5 kg, about 200 g to about 5 kg, about 250 g to about 5 kg, about 300 g to about 5 kg, about 400 g to about 5 kg, about 500 g to about 5 kg, about 10 g to about 1 kg, about 15 g to about 1 kg, about 20 g to about 1 kg, about 25 g to about 1 kg, about 30 g to about 1 kg, about 40 g to about 1 kg, about 50 g to about 1 kg, about 75 g to about 1 kg, about 100 g to about 1 kg, about 150 g to about 1 kg, about 200 g to about 1 kg, about 250 g to about 1 kg, about 300 g to about 1 kg, about 400 g to about 1 kg, or about 500 g to about 1 kg.

A method may comprise combining a microwave absorbing composition and a plant material at a ratio (mass:mass) of about 10:1 to about 1:100 such as about 10:1 to about 5:1, about 10:1 to about 1:1, about 5:1 to about 1:1, about 5:1 to about 1:2, about 2:1 to about 1:1, about 2:1 to about 1:2, about 1:1 to about 1:2, about 1:1 to about 1:3, about 1:1 to about 1:4, about 1:1 to about 1:5, about 1:1 to about 1:10, about 1:1 to about 1:20, about 3:2 to about 2:3, about 3:2 to about 1:1, about 3:2 to about 1:3, about 2:3 to about 1:3, about 2:3 to about 1:1, about 1:2 to about 1:3, about 1:2 to about 1:4, about 1:2 to about 1:5, about 1:3 to about 1:4, about 1:3 to about 1:5, about 1:3 to about 1:10, about 1:4 to about 1:5, about 1:4 to about 1:10, about 1:5 to about 1:10, about 1:5 to about 1:20, about 1:5 to about 1:25, about 1:10 to about 1:20, about 1:10 to about 1:50, about 1:10 to about 1:100, about 1:20 to about 1:100, or about 1:50 to about 1:100, e.g., about 10:1, 5:1, 4:1, 3:1, 2:1, 3:2, 4:3, 5:4, 1:1, 4:5, 3:4, 2:3, 1:2, 1:3, 1:4, 1:5, 1:6, 1:7, 1:8, 1:9, 1:10, 1:20, 1:25, 1:30, 1:40, 1:50, or 1:100.

A microwave absorbing composition typically lacks compounds having a boiling point that is less than the boiling point of the plant oil. For example, a microwave absorbing composition typically lacks compounds having a boiling point less than about 300° F., about 310° F., about 314° F., about 320° F., about 330° F., about 340° F., about 350° F., about 360° F., about 370° F., about 380° F., about 390° F., about 400° F., about 410° F., about 420° F., about 430° F., about 440° F., or about 450° F. The precise boiling point of the compounds that make up a microwave absorbing composition is not particularly limiting so long as each compound has a boiling point that is greater than the boiling point of the plant oil. The boiling point of water in comparison is 212° F.

A microwave absorbing composition typically has an autoignition temperature that is greater than the boiling point of the plant oil. For example, a microwave absorbing composition may have an autoignition temperature greater than about 360° F., about 370° F., about 380° F., about 390° F., about 400° F., about 410° F., about 420° F., about 430° F., about 440° F., or about 450° F. The precise autoignition temperature of the microwave absorbing composition is not particularly limiting so long as it is greater than the boiling point of the plant oil.

I. Cartridges

A system may comprise one or more removable cartridges. A removable cartridge is typically configured to contain a primed plant material (i.e., a mixture comprising plant material and a microwave absorbing agent or microwave absorbing composition). A removable cartridge may comprise primed plant material. A removable cartridge is preferably shaped and sized to allow the removable cartridge to enter and exit the extraction chamber, e.g., via a first opening of the extraction chamber. A removable cartridge includes external walls, and the external walls of a removable cartridge may slidably engage the internal walls of an extraction chamber. In this way, a removable cartridge can facilitate the insertion and/or removal of the cartridge and/or primed plant material into and out of the extraction chamber.

A removable cartridge contains an opening that allows volatized oil to exit the cartridge. A removable cartridge contains either an opening that allows the transmission of microwave radiation into the cartridge or a wall that is transparent to the transmission of microwave radiation at a frequency capable of dielectrically heating a microwave absorbing agent and/or heating the microwave absorbing agent by interfacial or Maxwell-Wagner-Sillars polarization.

A removable cartridge is optionally configured to allow for the rotation, stirring, or shaking of primed plant material within it.

A system may comprise a sealing puck, e.g., wherein the sealing puck is configured to seal at least a portion of an opening to the removable cartridge. For example, the removable cartridge may comprise a single opening, the plant material and microwave absorbing agent/composition may be inserted into the removable cartridge through the single opening, and the single opening may be sealed with the sealing puck. The sealing puck may comprise an opening configured to direct volatized oil from within the removable cartridge into the cooling chamber. A filter as described herein may optionally be positioned between the sealing puck and the mixture of plant material and microwave absorbing agent/composition.

J. Methods

A method of the embodiments typically comprises providing a system for extracting oil from plant material, wherein the system comprises a microwave emitter, extraction chamber, and cooling chamber as described herein.

A method typically comprises combining a plant material and a microwave absorbing agent, thereby generating a primed plant material. Combining a plant material and microwave absorbing agent may comprise combining the plant material and a microwave absorbing composition comprising the microwave absorbing agent. Combining may refer to mixing or blending. "Combining" as the term is used herein refers to the positioning of a plant material in proximity to a microwave absorbing agent or microwave absorbing composition such that the agent or composition can heat the plant material either directly (e.g., through direct contact between either the agent or composition and the plant material such as by thermal radiation) and/or indirectly (e.g., by the circulation of gas between either the agent or composition and the plant material such as by convection). Combining preferably strikes a balance between maximizing the surface area of contact between the plant material and the microwave absorbing agent or composition and a need for voids in the primed plant material to allow volatized oil to exit the primed plant material.

A method typically comprises inserting the primed plant material into the extraction chamber of the system. Inserting the primed plant material into the extraction chamber may comprise inserting a cartridge comprising the primed plant material into the extraction chamber. The primed plant material may be inserted into the extraction chamber through a first opening of the extraction chamber.

A method may comprise closing a first opening of the extraction chamber, e.g., after inserting primed plant material into the extraction chamber. Closing may comprise sealing. An extraction chamber may be closed, for example, with a sealing puck. A sealing puck may be configured to seal the first opening of an extraction chamber thereby inhibiting volatized oil from exiting the extraction chamber through the first opening.

A method typically comprises irradiating a microwave absorbing agent with microwaves emitted from a microwave emitter, thereby dielectrically heating the microwave absorbing agent and/or heating the microwave absorbing agent by interfacial or Maxwell-Wagner-Sillars polarization, heating a plant oil, and volatizing the plant oil to produce a volatized oil. Heating the plant oil may be mediated by a microwave absorbing composition and/or plant material, e.g., by conduction, convection, and/or thermal radiation, although the precise mechanism of heating is not particularly limiting.

A method typically comprises heating the plant material to a temperature greater than the boiling point of the plant oil. The method may comprise heating the plant material to a temperature of about 50° F. to about 450° F. such as about 50° F. to about 100° F., about 50° F. to about 150° F., about 300° F. to about 450° F., about 314° F. to about 450° F., about 314° F. to about 427° F., about 314° F. to about 400° F., about 365° F. to about 450° F., about 365° F. to about 427° F., or about 365° F. to about 400° F. Heating preferably does not cause pyrolysis of the plant oil or plant material.

A method preferably comprises monitoring a temperature inside the extraction chamber. The method may comprise monitoring the temperature of the plant material inside the extraction chamber. The precise method of monitoring the temperature is not particularly limiting, and the temperature may be monitored using any known method, e.g., by monitoring a thermocouple disposed within the extraction chamber.

A method may comprise maintaining a vaporization temperature inside the extraction chamber. The vaporization temperature is preferably maintained above the boiling point of the plant oil and below the autoignition temperature of the plant material, e.g., below about 450° F. The vaporization temperature may be about 50° F. to about 450° F. such as about 50° F. to about 100° F., about 50° F. to about 150° F., about 300° F. to about 450° F., 314° F. to about 450° F., about 314° F. to about 427° F., about 314° F. to about 400° F., about 365° F. to about 450° F., about 365° F. to about 427° F., or about 365° F. to about 400° F. Maintaining a vaporization temperature preferably does not cause pyrolysis of the plant oil or plant material.

A method may comprise maintaining a temperature inside the extraction chamber at about 100° F. to about 300° F., about 100° F. to about 200° F., about 150° F. to about 250° F., or about 200° F. to about 300° F.

A method may comprise adjusting the power of the microwave radiation, e.g., to maintain a temperature within a specified range. Adjusting the power of the microwave radiation may comprise, for example, adjusting the intensity of the microwave radiation that irradiates the microwave absorbing agent and/or cycling the microwave radiation that irradiates the microwave absorbing agent on and off.

The method may comprise maintaining a vaporization temperature inside the extraction chamber for about 5 seconds to two minutes, such as 5 seconds to 30 seconds, 30 seconds to 45 seconds, 30 seconds to one minute, one minute to two minutes, or 2 minutes to about 5 hours such as about 2 minutes to about 120 minutes, about 4 minutes to about 60 minutes, about 8 minutes to about 40 minutes, about 2 minutes to about 10 minutes, about 5 minutes to about 15 minutes, about 10 minutes to about 20 minutes, about 15 minutes to about 30 minutes, or about 20 minutes to about 40 minutes.

A method may comprise altering the propagation direction of the microwave radiation in relation to the microwave absorbing agent, e.g., to evenly heat the plant oil and/or plant material. Altering the propagation direction may comprise, for example, stirring, shaking, or rotating the plant material and/or microwave absorbing agent/composition while the microwave absorbing agent is being irradiated. For example, the method may comprise rotating or shaking either the extraction chamber or a cartridge disposed within the extraction chamber. The method may comprise stirring the plant material and microwave absorbing agent/composition, e.g., with a stirrer such as a stirrer comprising one or more blades.

A method may comprise cooling and/or condensing the volatized oil in the cooling chamber. Cooling and/or condensing the volatized oil typically produces a condensed oil. Cooling and/or condensing is typically performed by directing the volatized oil to a surface of the cooling chamber wherein the surface has a temperature below the boiling point of the volatized oil. The cooling chamber may comprise at least one surface that has a temperature below the boiling point of the volatized oil.

In some embodiments, the temperature of the at least one surface is maintained at or above room temperature. Temperatures greater than room temperature typically reduce the viscosity of a condensed oil, which may provide advantages for the collection of the condensed oil. Room temperature is 70° F. as the term "room temperature" is used herein.

In some embodiments, the temperature of the at least one surface is maintained at or above the boiling point of water at the pressure contained inside the cooling chamber, i.e., 212° F. at atmospheric pressure or 15° F. at 99.7% vacuum, which may allow for the condensation of oil without condensation of water. In some embodiments, at least one surface may be maintained below the boiling point of water depending on the nature of the cooling chamber and volatized oil, for example, to increase the yield of condensed oil.

A method may comprise maintaining at least one surface of the cooling chamber at a temperature of about 70° F. to about 314° F., such as about 80° F. to about 314° F., about 100° F. to about 314° F., about 150° F. to about 314° F., about 200° F. to about 314° F., about 212° F. to about 314° F., about 250° F. to about 314° F., about 300° F. to about 314° F., about 80° F. to about 300° F., about 100° F. to about 300° F., about 150° F. to about 300° F., about 200° F. to about 300° F., about 212° F. to about 300° F., about 250° F.

to about 300° F., about 80° F. to about 250° F., about 100° F. to about 250° F., about 150° F. to about 250° F., about 200° F. to about 250° F., about 212° F. to about 250° F., about 80° F. to about 200° F., about 100° F. to about 200° F., about 150° F. to about 200° F., about 80° F. to about 150° F., about 100° F. to about 150° F., or about 80° F. to about 100° F.

A method may optionally further comprise applying a vacuum to the extraction chamber and/or removable cartridge.

A method may comprise maintaining at least one surface of the cooling chamber at a temperature of about 0° F. to about −325° F., such as about 0° F. to about −50° F., about 0° F. to about −100° F., or about −50° F. to about −150° F., e.g., wherein the method also includes applying a vacuum to the extraction chamber and/or removable cartridge. A method may comprise maintaining at least one surface of the cooling chamber at a temperature of about 50° F. to about 0° F., such as about 50° F. to about 30° F., about 40° F. to about 20° F., about 30° F. to about 10° F., or about 20° F. to about 0° F.

A method may comprise collecting at least a portion of the condensed oil, thereby producing a collected oil. A method may comprise collecting essentially all of the condensed oil. Collecting at least a portion of the condensed oil typically comprises transferring condensed oil from the surface(s) of a cooling chamber to a separate compartment, which may be accomplished passively (e.g., by gravity), mechanically (e.g., by a pump or blade), or manually (e.g., by opening the cooling chamber and removing the condensed oil from it).

A method may optionally comprise removing water from the condensed oil or collected oil. Water may be removed from the collected oil, for example, by heating the collected oil to a temperature greater than the boiling point of water (e.g., either at atmospheric pressure or with vacuum assistance to decrease the boiling point of the water), thereby evaporating water from the collected oil. Water may be removed by simply separating the aqueous phase from the collected oil.

A method according to the various embodiments described herein typically does not comprise steam distillation. In some embodiments, the mass of the plant oil that is volatized from the plant material is greater than the mass of water that is volatized from the plant material. The ratio of the mass of plant oil that is volatized from the plant material to the mass of water that is volatized from the plant material may be, for example, at least about 1:3, about 1:2, about 1:1, about 2:1, or about 3:1.

K. Collected Oil

A collected oil is a plant oil or a mixture of plant oils as the term "plant oil" is described herein. A collected oil is typically suitable for human consumption, e.g., because it has been purified from plant material by distillation. A collected oil typically does not contain organic solvent such as isobutane, ethanol, or chloroform. In some instances, a collected oil nevertheless contains trace ethanol as ethanol may be used to flush or clean the systems described herein. A collected oil may comprise, for example, cannabidiol and/or delta-9-tetrahydrocannabinol. At least about 5%, 10%, 15%, 20%, 30%, 40%, 50%, 60%, 70%, 80%, 85%, 90%, 96%, 97%, 98%, or 99% of a collected oil may consist of a form of cannabidiol and/or tetrahydrocannabinol or other cannabinoids.

L. Non-Limiting Exemplary System

As illustrated in the FIGURE, a system may include a microwave chamber 1, a microwave penetrable plant material cartridge 2, a mixture of plant material and a microwave absorbing agent 3 ("primed plant material") contained within the plant material cartridge 2, a microwave shielding end 4 of the plant material cartridge that facilitates insertion from a first opening of the microwave chamber, a filter pad 5 that may be placed within or adjacent to the plant material cartridge 2, a sealing surface 6 that is in contact with the plant material cartridge 2 (or utilized as a lid/plug for the plant material cartridge 2), a vapor outlet 7 (e.g., second opening) that allows vapors to pass from within the plant material cartridge 2 and exit the microwave chamber 1, a vapor condenser 8, which may optionally be jacketed with a coolant, a condensed oil reservoir 9, a plant material cartridge temperature sensor 10, a cooling chamber temperature sensor 11, and a microwave emitter 12.

To operate the invention depicted in the FIGURE, an empty plant material cartridge 2 is placed on a flat surface with the microwave shielding end 4 down. The plant material cartridge 2 is filled with a mixture of plant material and a microwave absorbing agent 3 to provide a primed plant material. The microwave absorbing agent may comprise one or more various types of polar substrates such as substrates containing ions and/or dipoles, or any other substance or substrate that is excited by microwave radiation. Once the plant material cartridge 2 is filled with primed plant material 3, a filter 5, which may comprise glass fiber, is optionally placed on top of the primed plant material 3, and the primed plant material 3 is firmly packed. The plant material cartridge 2 is then inserted through the top of the microwave chamber 1 such that it is firmly in contact with the lower surface of the microwave chamber 1. A limit switch or locking device may be used to ensure that the plant material cartridge 2 is properly inserted into the microwave chamber 1.

Once inserted into the microwave chamber 1, the microwave emitter 12 emits microwave radiation into the plant material cartridge 2. The microwave radiation dielectrically heats the microwave absorbing agent, which heats the plant material. A microwave safe temperature sensor 10 is used to provide feedback to the microwave emitter controls to inhibit overheating or pyrolysis of the plant material and/or plant oil. As the plant material is heated, the plant oil within the plant material vaporizes and exits the plant material cartridge 2 through the vapor outlet 7 ("second opening"). The vaporized oil then contacts a surface of the vapor condenser 8, thereby allowing the vaporized oil to condense into a condensed oil. The temperature of the vapor condenser 8 may optionally be maintained at a temperature that is cool enough to condense the vaporized oil, yet hot enough to keep the condensed oil flowing. Alternatively, the temperature of the vapor condenser 8 may be kept relatively cold to capture the volatized oil, and then intermittently heated to allow the condensed oil to flow. The condensed oil flow from the vapor condenser 8 into an oil collection reservoir 9.

Those of skill in the art will recognize that the herein described embodiments of the present invention may be altered in other ways without departing from the scope or teaching of the present invention. Those of skill in the art will also recognize that various other portions of the electromagnetic spectrum may be used in place of microwaves and still fall within the scope of this invention. It is the following claims, including all equivalents, which define the scope of the invention.

The invention claimed is:

1. A method of extracting myrcene from plant material, comprising:

providing a system for extracting oil from plant material, wherein the system comprises (a) a microwave emitter, (b) an extraction chamber in communication with the microwave emitter such that microwave radiation emitted by the microwave emitter is directed into the extraction chamber, and (c) a cooling chamber in communication with the extraction chamber such that volatized myrcene in the extraction chamber is directed into the cooling chamber;

combining a microwave absorbing composition and a plant material at a ratio (mass:mass) of 1:1 to 1:20, being an amount of the composition relative to the plant material that is substantially greater than used in the microwave preparation of food, wherein the microwave absorbing composition comprises a microwave absorbing agent, and the microwave absorbing agent is a compound other than water;

inserting the plant material and the microwave absorbing agent into the extraction chamber;

irradiating the microwave absorbing agent with microwave radiation emitted from the microwave emitter, thereby dielectrically heating the microwave absorbing agent, heating the plant material, and volatizing myrcene from the plant material to produce the volatized myrcene;

condensing the volatized myrcene in the cooling chamber, thereby producing condensed myrcene; and collecting a portion or all of the condensed myrcene.

2. A method of extracting caryophyllene from plant material, comprising:

providing a system for extracting oil from plant material, wherein the system comprises (a) a microwave emitter, (b) an extraction chamber in communication with the microwave emitter such that microwave radiation emitted by the microwave emitter is directed into the extraction chamber, and (c) a cooling chamber in communication with the extraction chamber such that volatized caryophyllene in the extraction chamber is directed into the cooling chamber;

combining a microwave absorbing composition and a plant material at a ratio (mass:mass) of 1:1 to 1:20 being an amount of the composition relative to the plant material that is substantially greater than used in the microwave preparation of food, wherein the microwave absorbing composition comprises a microwave absorbing agent, and the microwave absorbing agent is a compound other than water;

inserting the plant material and the microwave absorbing agent into the extraction chamber;

irradiating the microwave absorbing agent with microwave radiation emitted from the microwave emitter, thereby dielectrically heating the microwave absorbing agent, heating the plant material, and volatizing caryophyllene from the plant material to produce the volatized caryophyllene;

condensing the volatized caryophyllene in the cooling chamber, thereby producing condensed caryophyllene; and collecting a portion of the condensed caryophyllene.

3. A method of extracting oil from plant material, comprising:

providing a system for extracting oil from plant material, wherein the system comprises (a) a microwave emitter, (b) an extraction chamber in communication with the microwave emitter such that microwave radiation emitted by the microwave emitter is directed into the extraction chamber, and (c) a cooling chamber in communication with the extraction chamber such that volatized oil in the extraction chamber is directed into the cooling chamber;

combining a microwave absorbing composition and a plant material at a ratio (mass:mass) of 1:1 to 1:20 being an amount of the composition relative to the plant material that is substantially greater than used in the microwave preparation of food, wherein the microwave absorbing composition comprises a microwave absorbing agent, and the microwave absorbing agent is a compound other than water;

inserting the plant material and the microwave absorbing agent into the extraction chamber;

irradiating the microwave absorbing agent with microwave radiation emitted from the microwave emitter, thereby dielectrically heating the microwave absorbing agent, heating the plant material, and volatizing a plant oil from the plant material to produce the volatized oil;

condensing the volatized oil in the cooling chamber, thereby producing a condensed oil; and collecting a portion or all of the condensed oil, thereby producing a collected oil.

4. The method of claim 3, wherein the volatized oil, condensed oil, and collected oil comprise each of linalool, caryophyllene, myrcene, limonene, humulene, and pinene.

5. The method of claim 3, wherein the volatized oil, condensed oil, and collected oil comprise two or more of linalool, caryophyllene, myrcene, limonene, humulene, and pinene.

6. The method of claim 3, wherein the volatized oil, condensed oil, and collected oil comprise each of linalool, caryophyllene, and pinene.

7. The method of claim 3, wherein the volatized oil, condensed oil, and collected oil comprise each of linalool, limonene, and pinene.

8. The method of claim 3, wherein the volatized oil, condensed oil, and collected oil comprise each of linalool, myrcene, and pinene.

9. The method of claim 3, wherein the volatized oil, condensed oil, and collected oil comprise caryophyllene.

10. The method of claim 3, wherein the volatized oil, condensed oil, and collected oil comprise myrcene.

11. The method of claim 3, wherein the volatized oil, condensed oil, and collected oil comprise limonene.

12. The method of claim 3, wherein the volatized oil, condensed oil, and collected oil comprise humulene.

13. The method of claim 3, wherein the volatized oil, condensed oil, and collected oil comprise pinene.

14. The method of claim 3, wherein the method comprises volatizing a mass of water from the plant material; and the mass of plant oil that is volatized from the plant material is greater than the mass of water that is volatized from the plant material.

15. The method of claim 3, wherein the method comprises volatizing a mass of water from the plant material; and the ratio of the mass of plant oil that is volatized from the plant material to the mass of water that is volatized from the plant material is at least 2:1.

16. The method of claim 3, wherein the plant material consists of less than 10% water by weight.

17. The method of claim 3, wherein the boiling point of the plant oil is greater than 212° F.; and the microwave absorbing agent has a boiling point of greater than 360° F. at atmospheric pressure.

18. The method of claim 3, further comprising maintaining a temperature inside the extraction chamber of at least 300° F. and no greater than 450° F.

19. The method of claim 3, further comprising maintaining at least one surface of the cooling chamber at a temperature of 0 degrees Fahrenheit to −350 degrees Fahrenheit.

20. The method of claim 3, wherein inserting the plant material and the microwave absorbing agent into the extraction chamber comprises inserting a cartridge comprising the plant material and the microwave absorbing agent into the extraction chamber.

* * * * *